United States Patent
Alimonti et al.

(10) Patent No.: US 11,168,134 B2
(45) Date of Patent: Nov. 9, 2021

(54) METHODS OF TREATING ANDROGEN DEPRIVATION THERAPY RESISTANT PROSTATE CANCER

(71) Applicants: Fondazione per l'Istituto Oncologico di Ricerca (IOR), Bellinzona (CH); The Institute of Cancer Research: Royal Cancer Hospital, London (GB)

(72) Inventors: Andrea Alimonti, Bellinzona (CH); Arianna Calcinotto, Bellinzona (CH); Johann de Bono, London (GB)

(73) Assignees: FONDAZIONE PER L'ISTITUTO ONCOLOGICO DI RICERCA (IOR), Bellinzona (CH); THE INSTITUTE OF CANCER RESEARCH: ROYAL CANCER HOSPITAL, London (GB)

( * ) Notice: Subject to any disclaimer, the term of this patent is extended or adjusted under 35 U.S.C. 154(b) by 0 days.

(21) Appl. No.: 16/574,828

(22) Filed: Sep. 18, 2019

(65) Prior Publication Data
US 2020/0095314 A1    Mar. 26, 2020

Related U.S. Application Data

(60) Provisional application No. 62/734,002, filed on Sep. 20, 2018.

(51) Int. Cl.
*A61K 39/395* (2006.01)
*C07K 16/24* (2006.01)
*A61K 31/4166* (2006.01)
*A61K 31/506* (2006.01)
*G01N 33/574* (2006.01)
*C12Q 1/6886* (2018.01)
*A61K 39/00* (2006.01)

(52) U.S. Cl.
CPC ........ *C07K 16/244* (2013.01); *A61K 31/4166* (2013.01); *A61K 31/506* (2013.01); *A61K 39/3955* (2013.01); *C12Q 1/6886* (2013.01); *G01N 33/57434* (2013.01); *A61K 2039/505* (2013.01); *C12Q 2600/106* (2013.01); *C12Q 2600/158* (2013.01); *G01N 2333/54* (2013.01)

(58) Field of Classification Search
CPC .................................................. A61K 39/3955
See application file for complete search history.

(56) References Cited

PUBLICATIONS

Rudikoff et al. Proc. Natl. Acad. Sci. USA vol. 79, pp. 1979-1983 (Mar. 1982).*
Janeway et al. Immunology, 3rd ed., 1997, Garland Publications, Inc., p. 3:1-3:11.*
Jeon et al (2017), Human Vaccines and Immunotherapeutics, vol. 13, No. 10, pp. 2247-2259.*
Crawford et al (2018), Prostate Cancer and Prostatic Diseases, pp. 1-15, Springer Nature, https://doi.org/10.1038/s41391-018-0079-0.*
Alimonti, "Targeting Tumor-Infiltrating Myeloid Cells for Prostate Cancer Therapy," presented at the 2017 Annual Meeting of the American Association for Cancer Research on Dec. 5, 2017 (30 pages).
Calcinotto et al., "IL-23 secreted by myeloid cells drives castration-resistant prostate cancer," *Nature*, vol. 559, pp. 363-389, 2018 (27 pages, including supplemental materials).

* cited by examiner

*Primary Examiner* — Prema M Mertz
(74) *Attorney, Agent, or Firm* — Klarquist Sparkman, LLP

(57) ABSTRACT

The present invention provides a method of treatment of prostate cancer, comprising administering a therapeutically effective amount of an inhibitor of IL-23 and/or an inhibitor of IL-23R to a mammalian patient in need thereof. The prostate cancer may be castration resistant prostate cancer (CRPC). The inhibitor may, for example, be an anti-IL-23 antibody, such as risankizumab, guselkumab or tildrakizumab. The method of treatment may further comprise administration of androgen deprivation therapy, such as enzalutamide. Also provided is a method of predicting the development of resistance to androgen deprivation therapy (ADT) in a prostate cancer in a mammalian patient and a related screening method.

9 Claims, 19 Drawing Sheets

Specification includes a Sequence Listing.

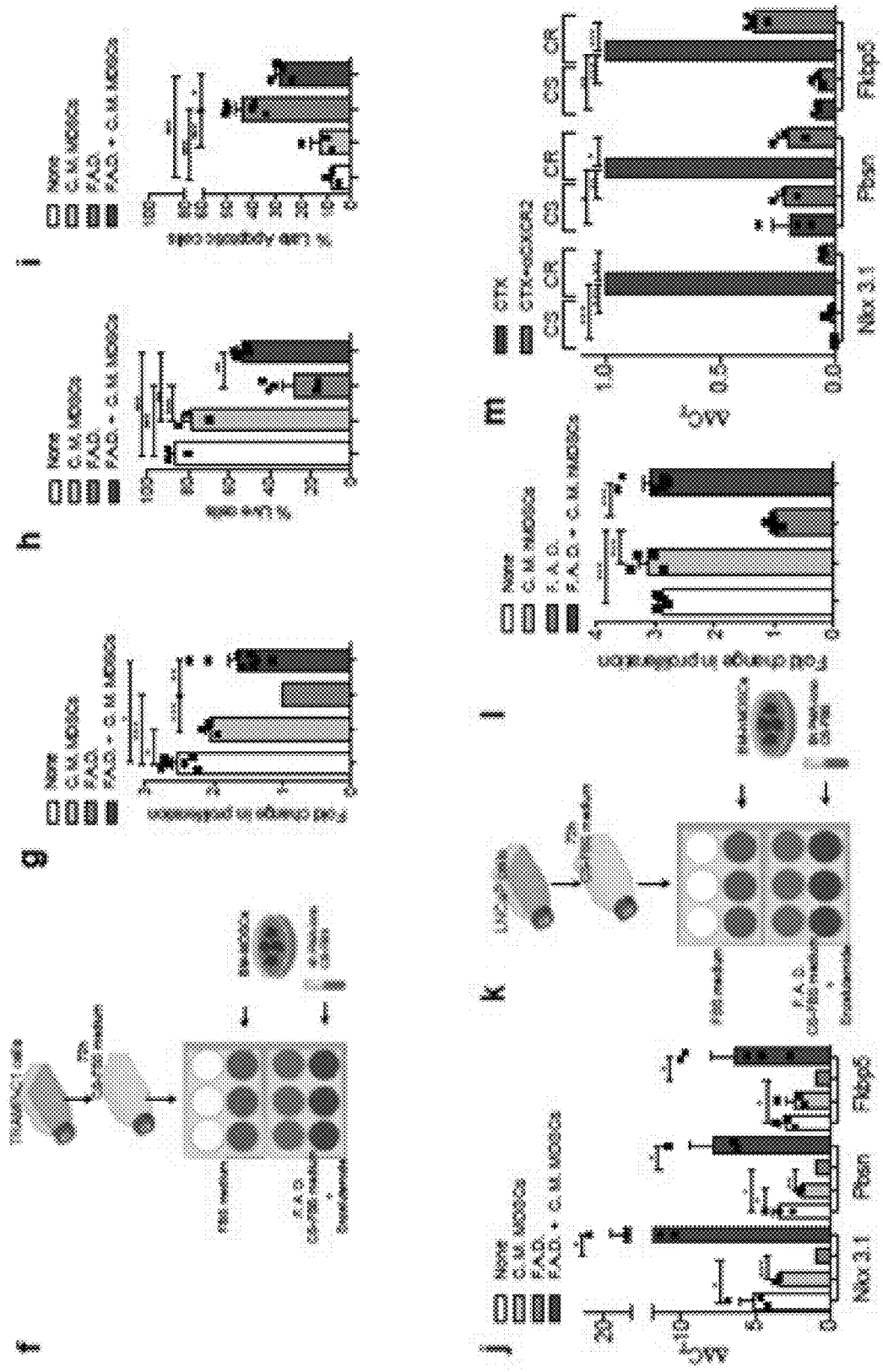
FIG. 1, cont.

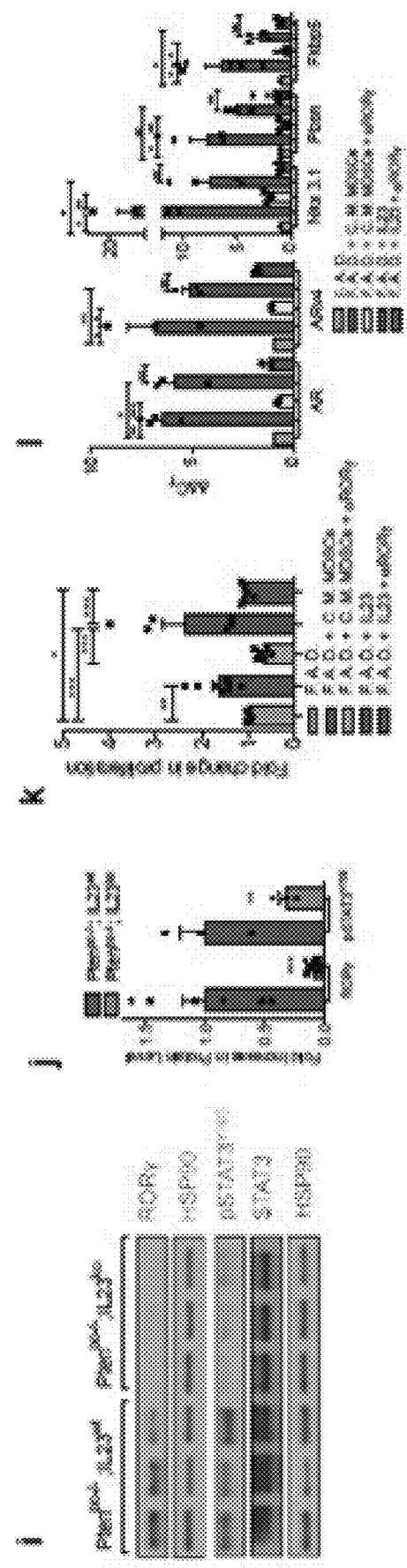
FIG. 3, cont.

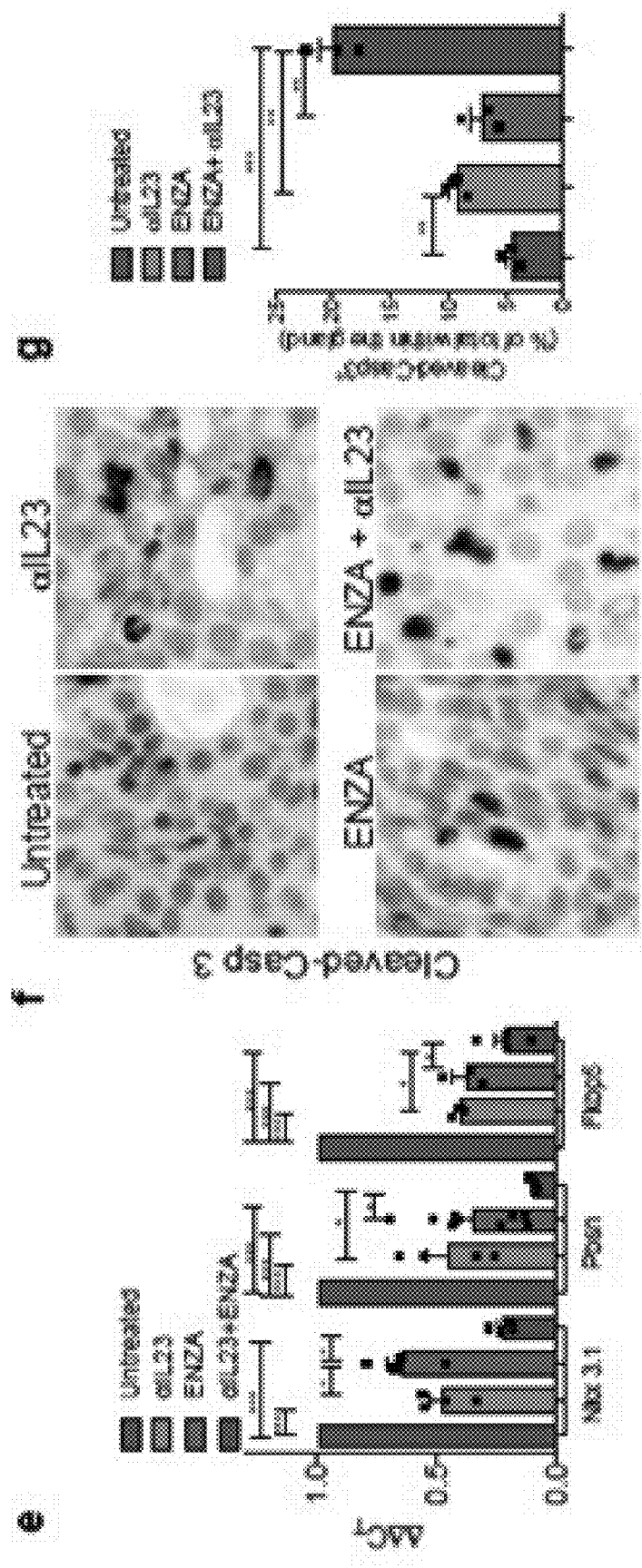
FIG. 4, cont.

FIG. 9, cont.
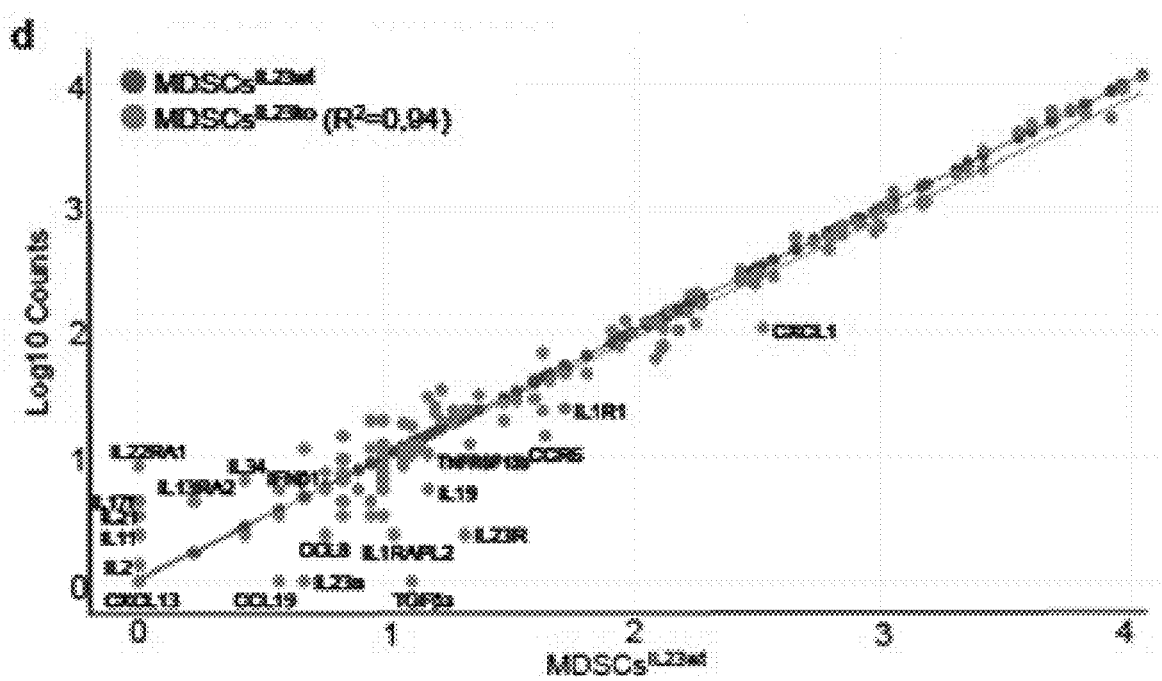
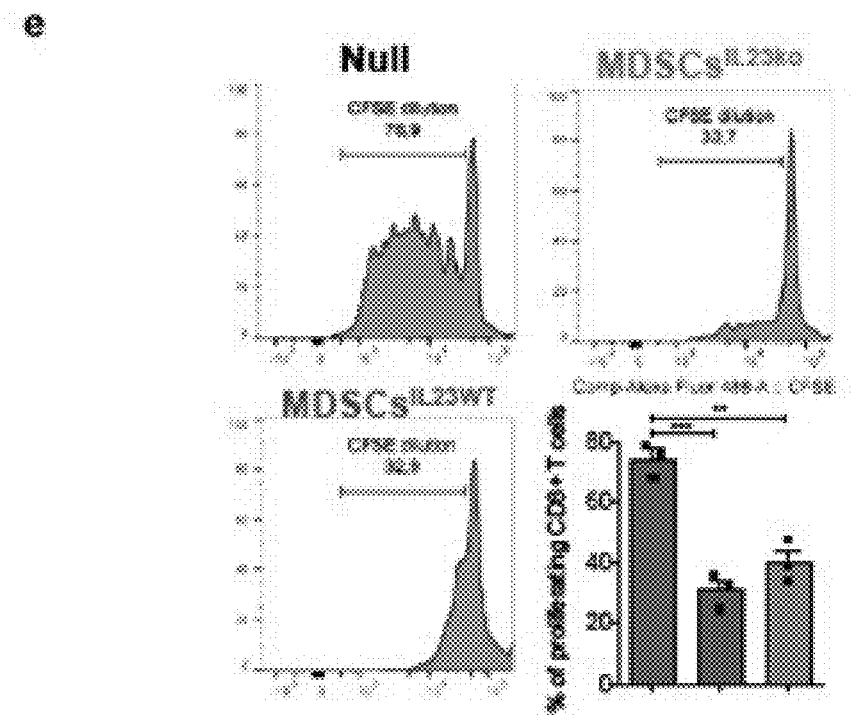

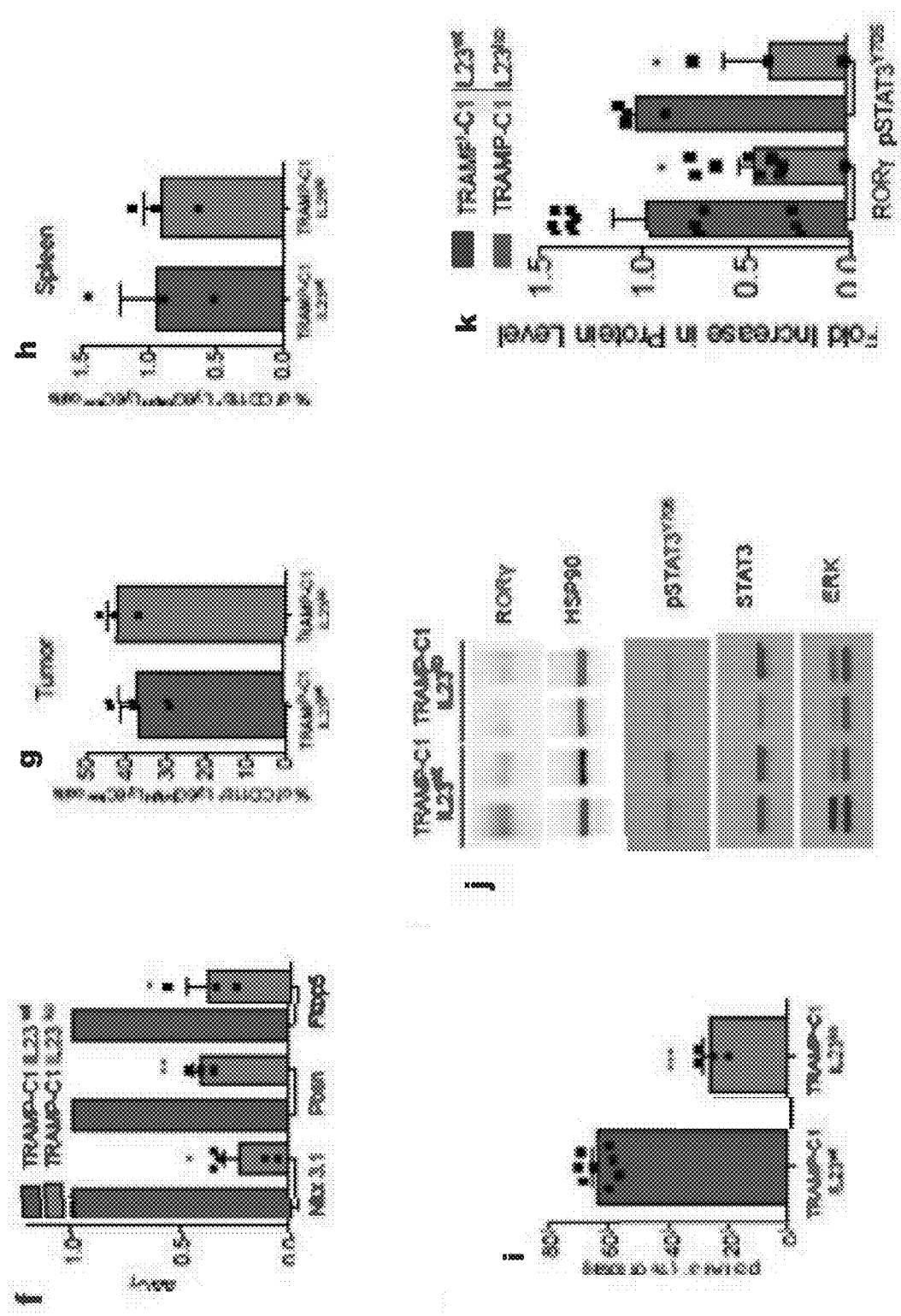
FIG. 11, cont.

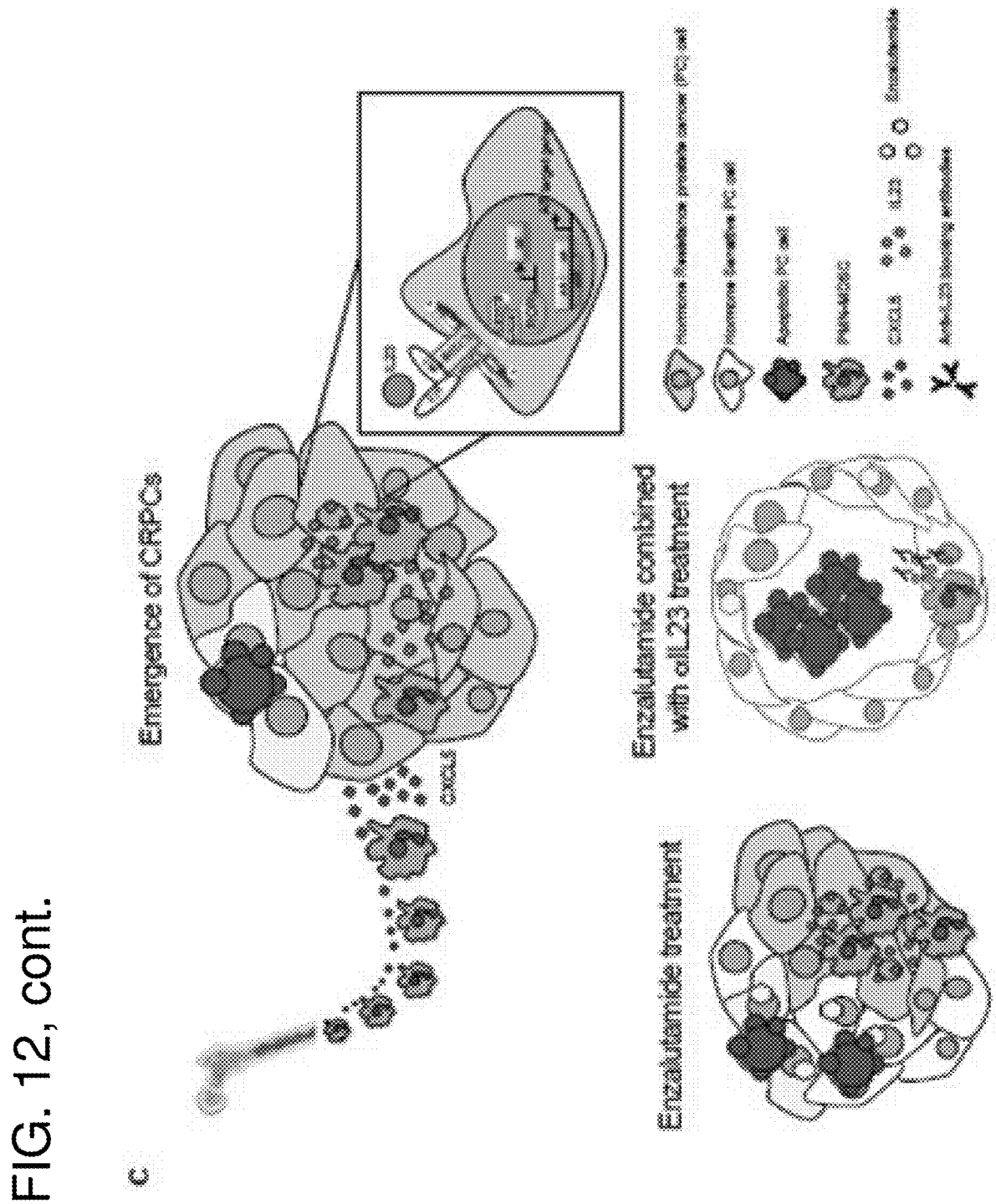
FIG. 12, cont.

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 1
ccactctcga ccctacatgg                                               20

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 2
ggcccccaaa gtgacattta tt                                            22

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 3
gctctgagac aatgaacgct                                               20

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 4
aaagagataa tctggctct                                                19

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 5
cctgtagccc acgtcgtag                                                19

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 6
gggagtagac aaggtacaac cc                                            22

<210> SEQ ID NO 7
<211> LENGTH: 21
<212> TYPE: DNA
<213> ORGANISM: Artificial Sequence

```
<220> FEATURE:
<223> OTHER INFORMATION: Synthetic oligonucleotide primer

<400> SEQUENCE: 7
gctcttactg actggcatga g                                              21

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 8
cgcagctcta ggagcatgtg                                                20

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 9
ctcccgtggc ttctagtgc                                                 19

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 10
gccttagttt ggacaggatc tg                                             22

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 11
aggtcggtgt gaacggattt g                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 12
tgtagaccat gtagttgagg t                                              21

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 13
ccagcagctc tctcggaatc                                                20
```

```
<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 14
tcatatgtcc cgctggtgc                                                    19
```

METHODS OF TREATING ANDROGEN DEPRIVATION THERAPY RESISTANT PROSTATE CANCER

CROSS REFERENCE TO RELATED APPLICATIONS

This application claims the benefit of U.S. Provisional Application No. 62/734,002, filed Sep. 20, 2018, which is herein incorporated by reference in its entirety.

FIELD OF THE INVENTION

The present invention relates to materials and methods for sensitising and treating cancers, including with combination therapy, and relates to methods for selecting and treating cancer patients.

BACKGROUND TO THE INVENTION

Sustained androgen receptor (AR) signalling is the primary driver of castration resistant prostate cancer (CRPC) and a primary target for therapeutic interventions [1]. However, after an initial response CRPC patients become resistant to androgen deprivation therapies (ADT). A better understanding of the mechanisms controlling the development of CRPC is a major clinical need [2-6]. Increased numbers of circulating and tumour-infiltrating myeloid-derived suppressor cells (MDSCs) have been observed in patients affected by different tumours including prostate cancer [8,9]. MDSCs are known to support tumorigenesis by either suppressing the antitumor immune response or by promoting angiogenesis and senescence evasion [10-12]. It has been reported that ROR-gamma drives androgen receptor expression and represents a therapeutic target in CRPC [22].

Despite advances in the treatment of prostate cancer, there remains a need for additional treatment choices, particularly treatment of CRPC which has become resistant to ADT. The present invention seeks to provide solutions to these needs and provides further related advantages.

BRIEF DESCRIPTION OF THE INVENTION

The present inventors have surprisingly found that interleukin 23 (IL-23) secreted by myeloid-derived suppressor cells confers castration resistance in prostate cancer and that treatments that inhibit the IL-23 pathway (such as inhibitors of IL-23 and/or IL-23R) oppose MDSCs-mediated castration insensitivity and synergize with standard of care ADT. Calcinotto et al., Nature, 2018, Vol. 559 (7714), pp. 363-369. doi: 10.1038/s41586-018-0266-0 is incorporated herein by reference in its entirety.

Accordingly, in a first aspect the present invention provides a method of treatment of prostate cancer, comprising administering a therapeutically effective amount of an inhibitor of interleukin 23 (IL-23) and/or an inhibitor of IL-23 receptor (IL-23R) to a mammalian patient in need thereof.

In some embodiments the prostate cancer comprises castration resistant prostate cancer (CRPC).

In some embodiments the method further comprises simultaneous, sequential or separate administration of androgen deprivation therapy (ADT) to the patient. In particular, ADT may comprise an anti-androgen therapy, such as an agent selected from the group consisting of: enzalutamide, cyproterone acetate, flutamide, nilutamide, bicalutamide, abiraterone acetate, seviteronel, apalutamide, darolutamide, and galeterone; a chemical castration agent, such as an agent selected from the group consisting of: leuprolide, goserelin, triptorelin, histrelin, degarelix, or a surgical form of ADT such as orchiectomy surgery.

In some embodiments the inhibitor of IL-23 and/or the inhibitor of IL-23R may be administered in sufficient amounts to sensitize the prostate cancer to the anti-tumor effects of said ADT and/or to reverse or reduce resistance (including acquired resistance) to ADT.

In some embodiments the inhibitor of IL-23 is an antibody that selectively binds IL-23 or a subunit thereof (e.g. p19 subunit), or is an antibody fragment that selectively binds IL-23 or a subunit thereof (e.g. p19 subunit).

In some embodiments the inhibitor of IL-23 is selected from the group consisting of: guselkumab (Janssen Biotech, Inc.), risankizumab (also known as BI 655066; Boehringer Ingelheim), and tildrakizumab (also known as MK-3222; Sun Pharmaceutical Industries Ltd.).

In some embodiments the method comprises administration of simultaneous, sequential or separate administration of said IL-23 inhibitor and enzalutamide.

In some embodiments the method further comprises simultaneous, sequential or separate administration of an inhibitor of interleukin 8 receptor (CXCR2), an inhibitor of RAR-related orphan receptor gamma (RORγ) and/or an inhibitor of Signal transducer and activator of transcription 3 (STAT3) to said patient.

In some embodiments said inhibitor of CXCR2 may be AZD5069 (AstraZeneca)).

In some embodiments said inhibitor of RORγ comprises an antibody or antibody fragment that selectively binds RORγ. Small molecule and peptide inhibitor of RORgamma have also been described (see, e.g., Huh and Littman, *Eur J Immunol.*, 2012, Vol. 42(9): 2232-2237) and are incorporated herein by reference.

In a related aspect the present invention provides a method of treatment of prostate cancer, comprising administering a therapeutically effective amount of an inhibitor of STAT3 to a mammalian patient in need thereof.

In a second aspect the present invention provides a method of reversing resistance to androgen deprivation therapy (ADT) in a prostate cancer, comprising:
  identifying a prostate cancer in a mammalian patient which prostate cancer has developed resistance to the anti-tumor effects of ADT; and
  administering a therapeutically effective amount of an inhibitor of interleukin 23 (IL-23) and/or an inhibitor of IL-23 receptor (IL-23R) to the patient. In some embodiments the a method further comprises administering ADT to the patient, for example, continuing or restarting ADT.

In some embodiments the method further comprises simultaneous, sequential or separate administration of an inhibitor of interleukin 8 receptor (CXCR2), an inhibitor of RAR-related orphan receptor gamma (RORγ) and/or an inhibitor of Signal transducer and activator of transcription 3 (STAT3) to said patient.

In a third aspect the present invention provides a method of predicting the development of resistance to androgen deprivation therapy (ADT) in a prostate cancer in a mammalian patient, comprising:
  (a) measuring IL-23 protein and/or IL-23 gene expression in a sample obtained the patient prior to, at the start of, or during ADT;

(b) measuring IL-23 protein and/or IL-23 gene expression in a sample obtained from the patient at a time subsequent to (a); and (c) predicting the development of resistance to ADT in the prostate cancer based on an increased level of IL-23 protein or IL-23 gene expression measured in (b) relative to (a).

In some embodiments the sample measured in (a) and the sample measured in (b) comprise blood or plasma samples. The present inventors measured elevated IL-23 protein levels in plasma samples obtained from CRPC patients relative to hormone sensitive prostate cancer (HSPC) patients (see, e.g., FIG. 2(d) ***P<0.001).

In some embodiments the sample measured in (a) and the sample measured in (b) comprise myeloid-derived suppressor cells (MDSCs) obtained from the tumor microenvironment of the prostate cancer.

In a related aspect, the method of the present invention may be for identifying patients that predicted to benefit from therapy targeting MDSCs and/or targeting IL23 (or IL23R). In particular embodiments, a tumor sample from a patient affected by prostate cancer may be dissociated and MDSCs collected, e.g., on a dish. The MDSCs may then be stimulated, e.g. for 3 hours, to produce secreted factors. Media into which the MDSCs have secreted factors (conditioned media) may be collected and used to culture prostate tumor cells from available cell lines or tumor organoids kept in androgen deprivation (i.e. in the presence of ADT). Patients whose MDSCs stimulate the growth of tumor cells or tumor organoids in vitro may thereby be identified as suitable for treatment with MDSC-targeting therapy and/or IL23 targeting therapy (e.g. an inhibitor of IL23 and/or an inhibitor of IL23R).

In some embodiments the method further comprises, having predicted development of resistance to ADT in the prostate cancer in (c), administering a therapeutically effective amount of an inhibitor of interleukin 23 (IL-23) and/or an inhibitor of IL-23 receptor (IL-23R to the patient. Also contemplated herein a treatment monitoring methods wherein, during ADT treatment of prostate cancer, IL-23 levels (e.g. in the tumor microenvironment, particularly MDSC-derived IL-23 adjacent to the prostate cancer cells or IL-23 in blood or plasma), are measured at multiple time points. An increase in said IL-23 levels is considered to be a sign of potential ADT resistance and may be followed-up with a method of the second aspect of the invention, e.g., administering an anti-IL-23 antibody in order to combat the ADT resistance.

In some embodiments the a method further comprises administering ADT to the patient, for example, continuing or restarting ADT.

In some embodiments the method further comprises simultaneous, sequential or separate administration of an inhibitor of interleukin 8 receptor (CXCR2), an inhibitor of RAR-related orphan receptor gamma (RORγ) and/or an inhibitor of Signal transducer and activator of transcription 3 (STAT3) to said patient.

In a fourth aspect the present invention provides a method of screening a candidate agent for anti-prostate cancer activity, comprising:
  (i) providing a candidate agent that inhibits interleukin 23 (IL-23) and/or IL-23 receptor (IL-23R);
  (ii) providing a non-human test animal that has at least one prostate cancer cell;
  (iii) treating the test animal with the candidate agent; and
  (iv) determining whether the candidate agent has a therapeutic effect on the at least one prostate cancer cell.

In some embodiments the at least one prostate cancer cell comprises a castration resistant prostate cancer (CRPC) tumor.

In some embodiments treating the test animal with the candidate agent further comprises treating the test animal with androgen deprivation therapy (ADT).

In some embodiments treating the test animal with the candidate agent further comprises treating the test animal with an inhibitor of interleukin 8 receptor (CXCR2), an inhibitor of RAR-related orphan receptor gamma (RORγ) and/or an inhibitor of Signal transducer and activator of transcription 3 (STAT3).

In some embodiments the test animal may be a laboratory rodent, such as a mouse or a rat. In particular, the test animal may be a Pten$^{pc-/-}$ as previously described [17].

In some embodiments the candidate agent may comprise an anti-IL-23 antibody, an anti-IL-23R antibody, a peptide antagonist of IL-23R, e.g. a peptide as disclosed in Quiniou et al., *Am J Physiol Regul Integr Comp Physiol.*, 2014; Vol. 307(10), pp. R1216-30. doi: 10.1152/ajpregu.00540.2013, incorporated herein by reference or PTG-200 as disclosed in Cheng, Xiaoli et al., *Gastroenterology*, Vol. 152, Issue 5, S31, incorporated herein by reference or a small molecule antagonist of IL-23R.

In a fifth aspect the present invention provides a screening method to identify factors secreted by myeloid-derived suppressor cells (MDSCs) which may drive resistance to androgen deprivation therapy (ADT) in prostate cancer, comprising:
  (i) generation of bone marrow derived MDSCs or extraction of MDSCs from a patient biopsy;
  (ii) stimulation of the MDSCs obtained in step (i) and collection of media conditioned by the stimulated MDSCs;
  (iii) culturing at least one prostate cancer cell with the MDSC-conditioned media of step (ii) and an ADT agent;
  (iv) comparing the growth rate of said at least one cultured prostate cancer cell in step (iii) with the growth rate of at least one prostate cancer cell cultured with said ADT agent in cell culture media that has not been conditioned with stimulated MDSCs, wherein a faster rate of growth in (iii) than (iv) indicates that the stimulated MDSCs have secreted a factor that may drive resistance to ADT; and
  (v) having determined in step (iv) that the stimulated MDSCs have secreted a factor that may drive resistance to ADT, further comprising analysing the MDSC-condition media to identify at least one factor that may drive resistance to ADT.

In some embodiments a tumor samples from a patient having prostate cancer may be dissociated and MDSCs collected, e.g., on a dish. The MDSCs may then be stimulated, e.g., for 3 hours to produce secreted factors. The media containing factors secreted from the MDSCs (conditioned media) may then be collected and used to culture prostate tumor cells from available cell lines or tumor organoids kept in androgen deprivation (i.e. in the presence of ADT). Conditioned media that positively regulates (i.e. increases) the growth of tumor cells or tumor organoids in ADT may then be analysed using suitable analytical techniques. For example, ELISA or mass spec.

In accordance with any aspect of the present invention, the mammalian patient may be a human (e.g. an adult male), a companion animal (e.g. a dog or cat), a laboratory animal (e.g. a mouse, rat, rabbit, pig or non-human primate), a domestic or farm animal (e.g. a pig, cow, horse or sheep). Preferably, the subject is a human male.

Embodiments of the present invention will now be described by way of example and not limitation with reference to the accompanying figures. However various further aspects and embodiments of the present invention will be apparent to those skilled in the art in view of the present disclosure.

The present invention includes the combination of the aspects and preferred features described except where such a combination is clearly impermissible or is stated to be expressly avoided. These and further aspects and embodiments of the invention are described in further detail below and with reference to the accompanying examples and figures.

Figure 1:
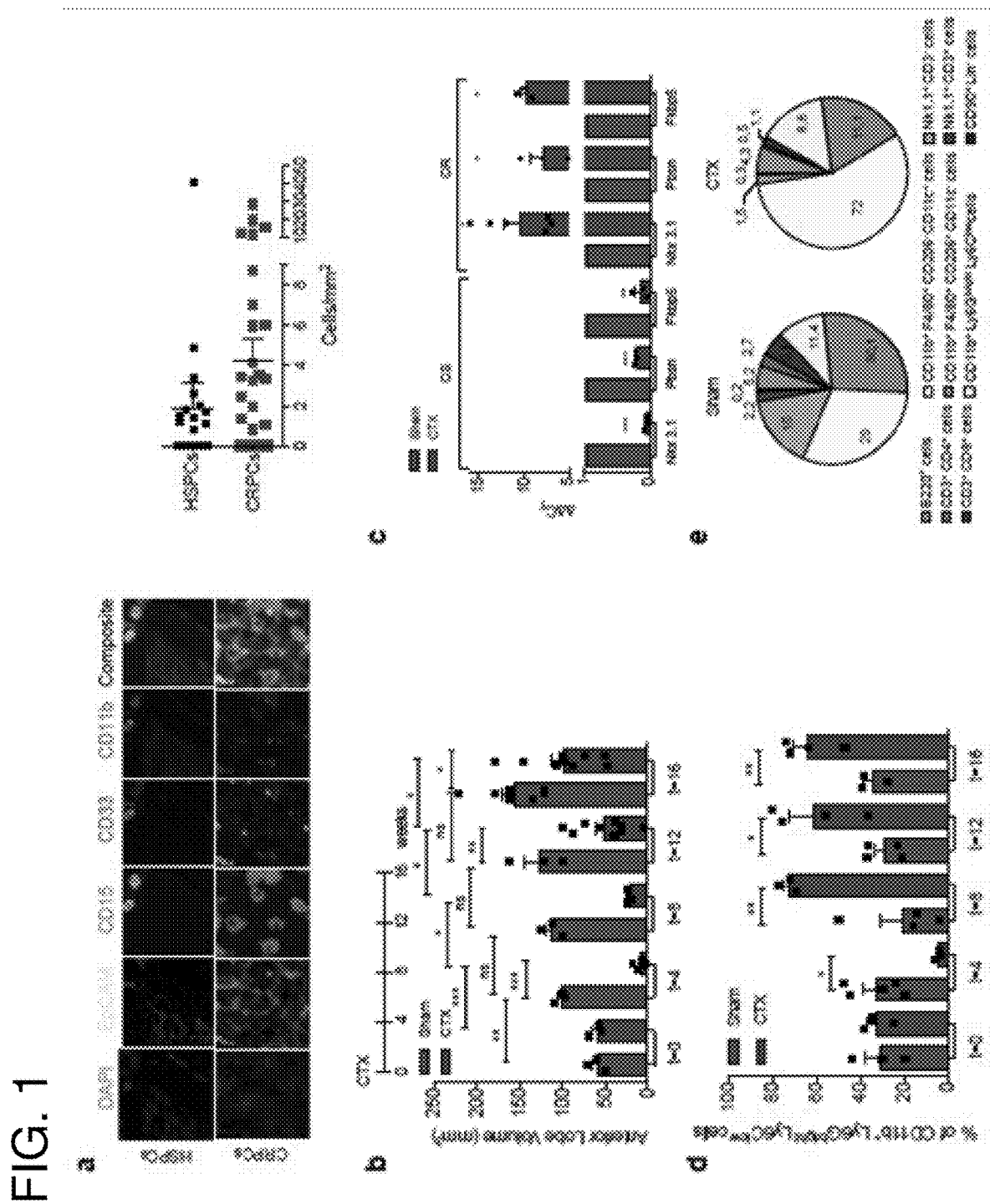
FIGS. 1A-1M: MDSCs infiltrate CRPC tumors and confer castration resistance. a, Multispectral microscopy images and quantification of the number of CD11b, CD33, CD15 (EpCAM yellow, CD15 green, CD33 red; CD11b pink) positive PMN-MDSCs within the tumor of hormone sensitive vs castration resistant prostate cancers (HSPCs, n=30 vs CRPCs, n=30). Cells were counterstained with the nuclear marker DAPI (blue). Statistical analyses (negative binomial regression model): P=0.005. b, c, d, Analysis of $Pten^{pc-/-}$ mice sham-operated (Sham) or $Pten^{pc-/-}$ mice after surgical castration (CTX) at different time points. b, Experimental set-up. Tumor volume of the anterior prostate lobe from Sham and CTX $Pten^{pc-/-}$ mice at the indicated time points is reported. c, qRT-PCR analyses of the indicated genes in the prostate tumors of Sham and CTX at t=4 (castration sensitive phase; CS) and t=12 (castration resistance phase; CR). d, Tumor PMN-MDSCs frequencies determined by flow cytometry (gated on $CD45^+$ cells). e, Percentages of various immune cell populations within the $CD45^+$-infiltrating immune cells in the prostate tumors from Sham and CTX $Pten^{pc-/-}$ mice assessed at 12 weeks after CTX by multiparametric flow cytometry analyses. b, c, d, e Aggregated data from three independent experiments are reported as mean±SE. Each dot represents an individual mouse. b, d, Statistical analyses (Unpaired Student t test): ns, not significant; *P<0.05; P<0.01; *P<0.001. (One-way Anova analyses of variance): P<0.001. c, Statistical analyses (Paired Student t test): *P<0.05; ***P<0.001. f, Experimental scheme. Briefly, TRAMP-C1 prostate cancer cells were starved in Charcoal Stripped FBS (CS-FBS) medium for 72 h and then cultured with normal medium or kept in full androgen deprivation medium (F.A.D.), with or without condition media obtained from activated BM-derived MDSCs (C.M. MDSCs). g, Cell proliferation of TRAMP-C1 cells after 72 h of co-culture (fold change compared with F.A.D. condition). h, Percentage of Annexin and 7AAD-negative TRAMP-C1 cells. i, Percentage of AnnexinV-positive and 7AAD-negative TRAMP-C1 cells. j, qRT-PCR analyses of the indicated genes in TRAMP-C1 cells after 24 h of co-culture (fold change compared with F.A.D. condition). g, h, i, j, Aggregated data from five independent experiments are reported as mean±SE. Each dot represents a biological replicate. k, Experimental scheme. l, Cell proliferation of LNCaP prostate cancer cells after 72 h of co-culture (fold change compared with F.A.D. condition). Aggregated data from three independent experiments are reported as mean±SE. Each dot represents a biological replicate. g, h, i, j, l, Statistical analyses (Unpaired Student t test): *P<0.05; P<0.01; *P<0.001. m, qRT-PCR analyses of the indicated genes in the prostate tumors of CTX $Pten^{pc-/-}$ mice treated or not with CXCR2 antagonist (αCXCR2) (n=3 per group). Statistical analyses (Paired Student t test): ***P<0.001.

b-e, Aggregated data from five independent experiments are reported as mean±SE. Each dot represents a biological replicate. b-d, Statistical analyses (Unpaired Student t test): *P<0.05; P<0.01; *P<0.001. e, Statistical analyses (Paired Student t test): *P<0.05; P<0.01; *P<0.001. f, g, Tumor MDSCs frequencies determined by flow cytometry and Tumor volume of prostate tumors of CTX $Pten^{pc-/-}$ mice treated or not with CXCR2 antagonist (αCXCR2). Aggregated data from two independent experiments are reported as mean±SE. Each dot represents an individual mouse. Statistical analyses (Unpaired Student t test): *P<0.05; P<0.01; *P<0.001. h, Cell proliferation of TRAMP-C1 cells after 72 h of treatment with CXCR2 antagonist (αCXCR2) i, qRT-PCR analyses of the indicated genes in TRAMP-C1 cells after 24 h of treatment (fold change compared with F.A.D. condition). h, i, Aggregated data from three independent experiments are reported as mean±SE, fold change compared with F.A.D. condition.

FIGS. 7A-7H. Impaired tumor recruitment of MDSCs enhances response to surgical castration in different allograft models of prostate cancers. a, Schematic representation of the experiment. Six-week-old C57BL/6 males were challenged s.c. with TRAMP-C1 cells. When tumors reached≈100 mm3, mice were surgically castrated and left untreated (CTX, n=8) or treated with CXCR2 antagonist (CTX+αCXCR2, n=9). Representative flow cytometry plots of PMN-MDSCs (CD11b$^+$ Ly6G$^+$ cells, gated on CD45$^+$ cells) in tumors for each experimental condition. b, qRT-PCR analyses of the indicated genes in the prostate tumors of CTX and CTX+αCXCR2 (n=3 per group). Statistical analyses (Paired Student t test): *P<0.05;*P<0.001. c, Average tumor volume (±SE) for each experimental group. Statistical analyses (Unpaired Student t test followed by Wilcoxon posttest): *P<0.001. d, Survival curves are reported in Kaplan-Meier plot. Statistical analyses (Long rank test): *P<0.001. e, Schematic representation of the experiment. Six-week-old FVB males were challenged s.c. with Myc-CaP cells. When tumors reached≈100 mm3, mice were surgically castrated and left untreated (CTX, n=5) or treated with CXCR2 antagonist (CTX+αCXCR2, n=5). Representative flow cytometry plots of PMN-MDSCs (CD11b+ Ly6G+ cells, gated on CD45+ cells) in tumors for each experimental condition. f, qRT-PCR analyses of the indicated genes in the prostate tumors of CTX and CTX+ αCXCR2 (n=3 per group). Statistical analyses (Paired Student t test): P<0.01; ***P<0.001. g, Average tumor volume (±SE) for each experimental group. Statistical analyses (Unpaired Student t test followed by Wilcoxon posttest): *P<0.05. h, Survival curves are reported in Kaplan-Meier plot. Statistical analyses (Long-rank test): **P<0.01.

FIGS. 8A-8F. IL23 pathway is the most up-regulated in the tumor upon castration. a, Gene expression of selected genes determined by NanoString nCounter gene expression assay in Sham $Pten^{pc-/-}$ and CTX $Pten^{pc-/-}$ tumors. Data are shown as pull of n=5. b, Analyses of the condition media of BM-derived MDSCs tested for the indicated soluble molecules by Mouse CytokineMAP B version 1.0. The graph reports the concentration of the indicated soluble molecules as Log 10 of the concentration found in the condition medium of BM-MDSCs, the values were subtracted of the background (culture medium). Data are shown as pull of n=10. c-d, IL23R protein level analyzed by flow cytometry and western blot on TRAMP-C1 cells under normal culture condition (FBS) or androgen deprivation culture condition (CS-FBS). Numbers indicate fold change in protein level. Loading control: anti-βactin antibody. e, qRT-PCR analyses of IL23 in the prostate tumors of castrated (CTX; n=6) or castrated and treated with CXCR2 antagonist (CTX+ αCXCR2; n=6) $Pten^{pc-/-}$ mice. mean±SE. c, e, Statistical analyses (Unpaired Student t test): P<0.001. f, Protein profile of the plasma of HSPC and CRPC patients. Data are analyzed as ratio between CRPC (pull of 18 samples) and HSPC (pull of 17 samples) and reported as fold increase in protein level.

FIGS. 9A-9E. IL23 and IL23 receptor levels increase in CRPC patients. a, b, IL23 and IL23R mRNA expression in the tumor of HSPCs and mCRPCs. c, Expression of IL23 in PMN-MDSC marker (CD11b, CD33, CD15) positive mCRPC patients. a-c, Statistical analyses (Unpaired Student t test) are reported. d, Correlation analyses of the gene expression of selected genes determined by NanoString nCounter gene expression assay in BM-MDSCs$^{IL23wt}$ and BM-MDSCs$^{IL23ko}$ reported by scatter plot analyses. Data are shown as pull of n=10. e, Representative flow cytometry plots of CFSE dilution (gated on CD8+ cells) and quantification of proliferating CD8+ T cells exposed to C.M. from BMMMDSCsIL23wt or BM-MDSCsIL23ko. Mean±SE. Each dot represents a biological replicate. Statistical analyses (Unpaired Student t test): P<0.01; *P<0.01.

Figure 10:
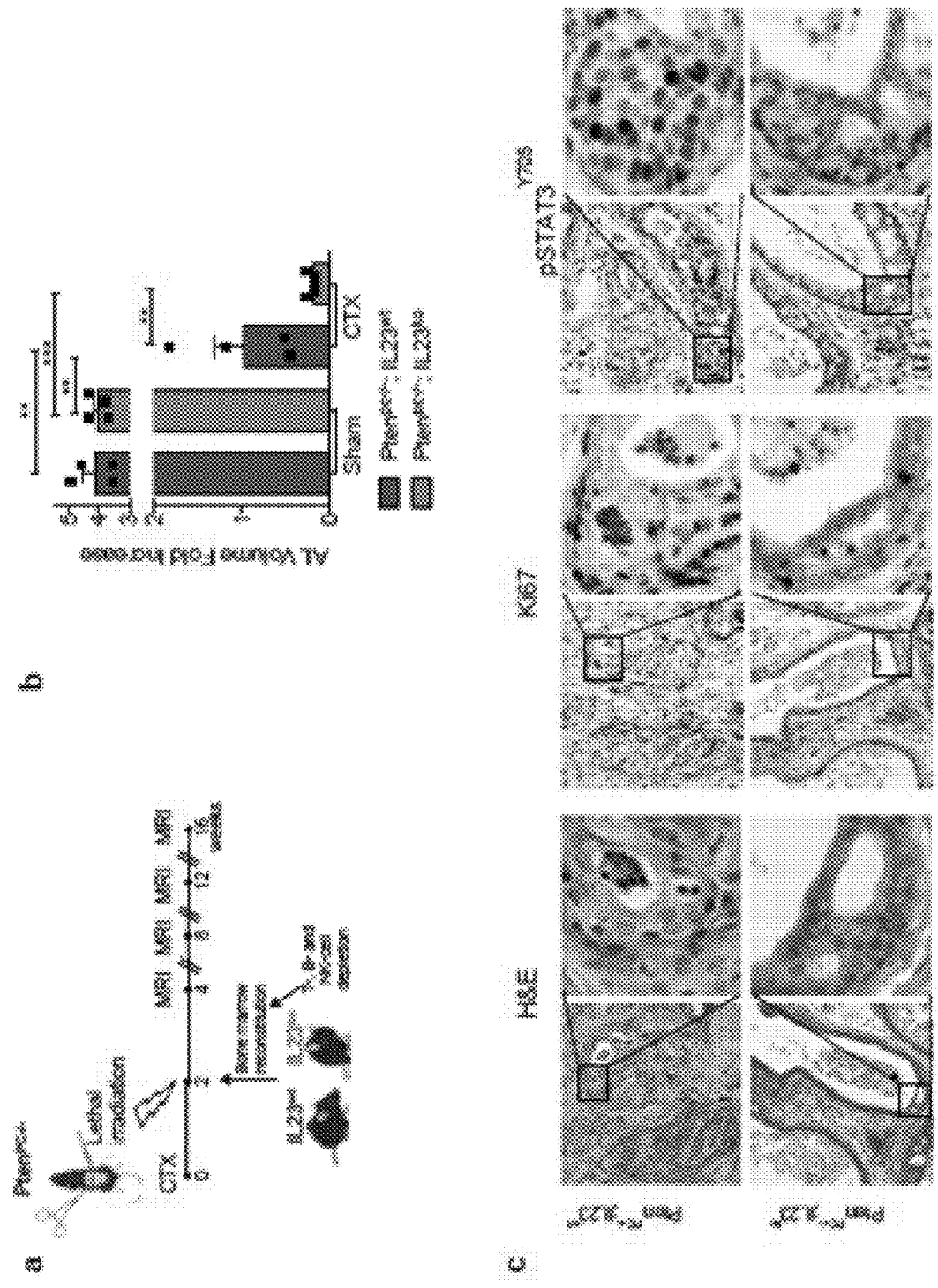

FIGS. 10A-10C. Genetic inhibition of IL23 limits castration resistance in $Pten^{pc-/-}$ mice in vivo. a, Experimental set-up. Sham-operated (Sham) or Castrated (CTX) $Pten^{pc-/-}$ mice were lethally irradiated and transplanted with BM precursors depleted by T, B, and NK cells from IL23wt and IL23ko mice. Then, monitored by MRI for tumor progression. b, Quantification of the tumor size of Sham-operated $Pten^{pc-/-}$; IL23wt (n=4) and $Pten^{pc-/-}$; IL23ko (n=4), and castrated $Pten^{pc-/-}$; IL23wt (n=4) and Ptenpc-/-; IL23ko (n=7) mice at completion of the study is reported as fold increase of the prostate anterior lobe (AL) volume (fold change compared with CTX $Pten^{pc-/-}$; IL23wt group). Data are reported as mean±SE. Statistical analyses (Unpaired Student t test): P<0.01, *P<0.001. c, H&E, Ki-67, and pSTAT3Y705 immunohistochemical staining (Ki-67 and pSTAT3$^{Y705}$ brown; nuclei, blue) of representative $Pten^{pc-/-}$; IL23wt and $Pten^{pc-/-}$; $IL23^{ko}$ mice at completion of the study. Original magnification, ×100 and ×400.

FIGS. 11A-11K. IL23 regulates castration resistance in the TRAMP-C1 allograft model. a, Schematic representation of the experiment. Six-week-old C57BL/6 males were lethally irradiated and transplanted with BM precursors from $IL23^{wt}$ and $IL23^{ko}$ mice. After the BM engraftment, the animals were challenged s.c. with TRAMP-C1 cells. When tumors reached ≈100 mm3, mice were surgically castrated and monitored for tumor progression. b, Average tumor volume (mean±SE) for each experimental group (n=8). Statistical analyses (Unpaired Student t test followed by Wilcoxon posttest): *P<0.05. c, Survival curves are reported in Kaplan-Meier plot. N=8. Statistical analyses (Long-rank test): *P<0.001. d, H&E, Ki-67 and pSTAT3$^{Y705}$ immunohistochemical staining (Ki-67 and pSTAT3$^{Y705}$ brown; nuclei, blue) of representative TRAMP-C1 $IL23^{wt}$ and TRAMP-C1 $IL23^{ko}$ bearing mice. Original magnification, X400. e, Quantification of Ki-67 positive cells is reported as a percentage of total. TRAMP-C1 $IL23^{wt}$ (n=8) and TRAMP-C1 $IL23^{ko}$ (n=4), one tumor per mouse, mean of three sections per mouse, ≥3 fields per section. Biological mean±SE. Statistical analyses (Unpaired Student t test): P<0.01. f, qRT-PCR analyses of the indicated genes in the tumors of TRAMP-C1 $IL23^{wt}$ (n=3) and TRAMP-C1 $IL23^{ko}$ (n=3) bearing mice at completion of the study. Data are reported as mean±SE. Statistical analyses (Paired Student t test): *P<0.05; P<0.01. g-h, PMN-MDSCs frequencies determined by flow cytometry in the tumor and in the spleen of TRAMP-C1 IL23$^{wt}$ (n=3) and TRAMP-C1 IL23$^{ko}$ (n=3) bearing mice 10 days after castration. Data are reported as mean±SE. i, Quantification of pSTAT3$^{Y705}$ reported as a percentage of total. TRAMP-C1 IL23wt (n=8) and TRAMP-C1 IL23ko (n=4), one tumor per mouse, mean of three sections per mouse, ≥3 fields per section. Biological mean±SE. Statistical analyses (Unpaired Student t test): *P<0.001. j, Western blot for RORΓ, pSTAT3$^{Y705}$ and total STAT3 levels of prostate tumors of TRAMP-C1 IL23wt and TRAMP-C1 IL23$^{ko}$ bearing mice. Loading control: HSP90 antibody or total ERK antibody. k, Quantification is reported as mean±SE. Each dot represents an individual mouse. Statistical analyses (Unpaired Student t test): *P <0.05.

Figure 12:
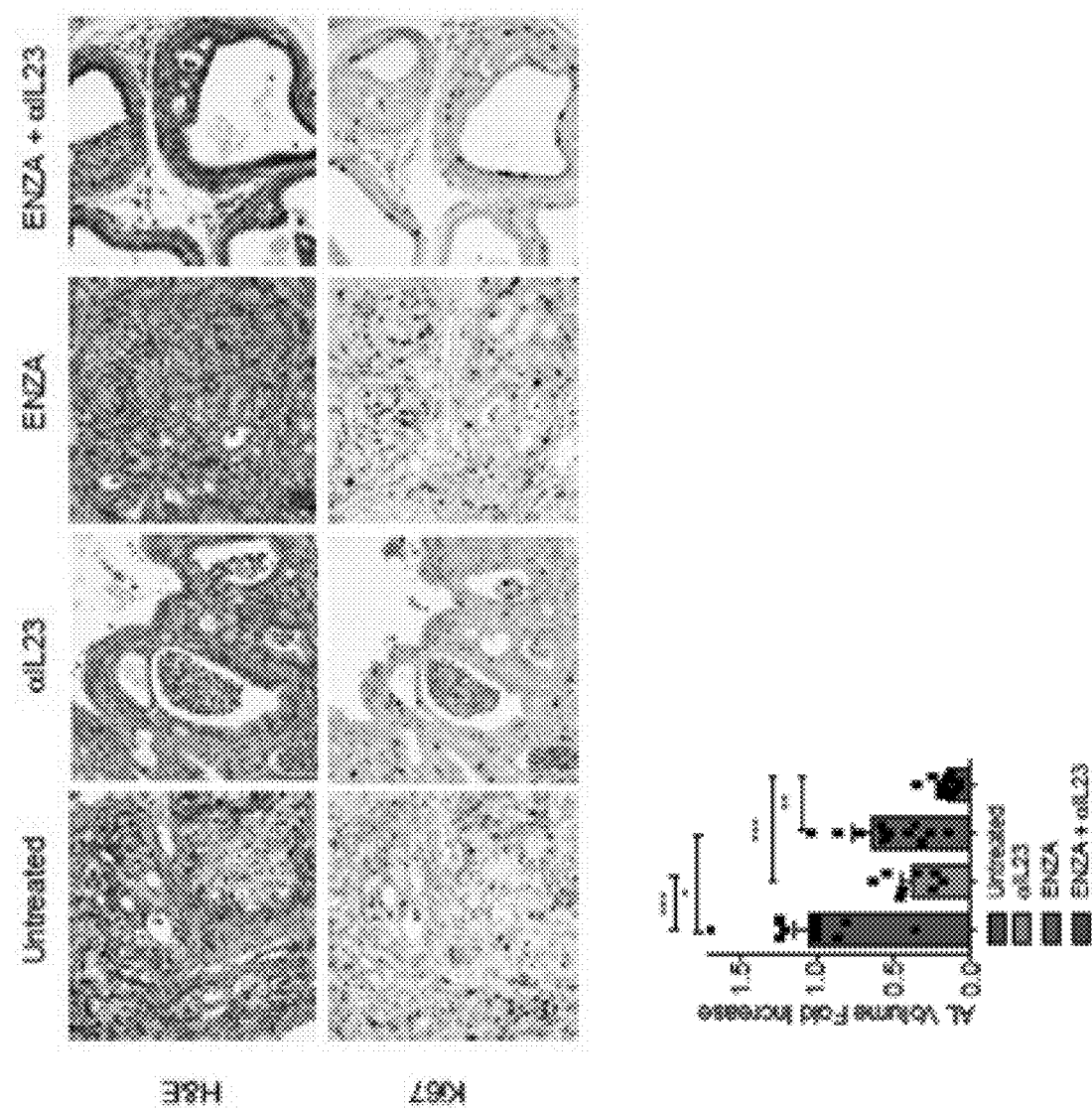

FIGS. 12A-12C. Pharmacological inhibition of IL23 in association with ADT delays disease progression in prostate cancer. a, H&E and Ki-67 immunohistochemical staining (Ki-67 brown; nuclei, blue) of representative castrated-Pten$^{pc-/-}$ mice treated with αIL23, ENZA or both. Original magnification, ×100. b, Quantification of the response to the treatments is reported as fold increase of the prostate anterior lobe (AL) volume (fold change compared with untreated group). Data are reported as mean±SE. Each dot represents an individual mouse. Statistical analyses (Unpaired Student t test): *P<0.05; P<0.01; *P<0.001. c, Upon castration, PMN-MDSCs progressively infiltrate the tumor bed mainly recruited by CXCL5. Within the tumor, PMN-MDSCs start to produce higher amount of IL23, thus establishing a positive-feedback loop that induce the over-expression of IL23R on the tumor epithelial cells, and confer castration resistance by activating the STAT3/RORγ pathway. Enzalutamide treatment can block androgen receptor inducing sensitiveness of prostate cancer cells to androgen deprivation, but the persistence presence of PMN-MDSCs-derived IL23 rescues the drug sensitiveness leading to androgen deprivation resistance. Anti-IL23 treatment reverts castration resistance in prostate cancer enhancing the efficacy of enzalutamide.

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

In describing the present invention, the following terms will be employed, and are intended to be defined as indicated below.

As used herein, the term "tissue" (for example in the context of "a control sample obtained from a cancer-free tissue") may be given a broad interpretation, in particular, specifically including any one or more cells, a biopsy of a solid tissue, or a biological liquid (e.g. blood, plasma, cerebrospinal fluid, urine or faeces) that contains the protein or nucleic acid of interest. Nevertheless, in certain cases, "tissue" may be taken to mean an ensemble of similar cells from the same origin that together carry out a specific function.

Antibody Molecule

As used herein with reference to all aspects of the invention, the term "antibody" or "antibody molecule" includes any immunoglobulin whether natural or partly or wholly synthetically produced. The term "antibody" or "antibody molecule" includes monoclonal antibodies (mAb) and polyclonal antibodies (including polyclonal antisera). Antibodies may be intact or fragments derived from full antibodies (see below). Antibodies may be human antibodies, humanised antibodies or antibodies of non-human origin. "Monoclonal antibodies" are homogeneous, highly specific antibody populations directed against a single antigenic site or "determinant" of the target molecule. "Polyclonal antibodies" include heterogeneous antibody populations that are directed against different antigenic determinants of the target molecule. The term "antiserum" or "antisera" refers to blood serum containing antibodies obtained from immunized animals.

It has been shown that fragments of a whole antibody can perform the function of binding antigens. Thus reference to antibody herein, and with reference to the methods, arrays and kits of the invention, covers a full antibody and also covers any polypeptide or protein comprising an antibody binding fragment. Examples of binding fragments are (i) the Fab fragment consisting of $V_L$, $V_H$, $C_L$ and $C_H1$ domains; (ii) the Fd fragment consisting of the $V_H$ and $C_H1$ domains; (iii) the Fv fragment consisting of the $V_L$ and $V_H$ domains of a single antibody; (iv) the dAb fragment which consists of a $V_H$ domain; (v) isolated CDR regions; (vi) F(ab')$_2$ fragments, a bivalent fragment comprising two linked Fab fragments (vii) single chain Fv molecules (scFv), wherein a $V_H$ domain and a $V_L$ domain are linked by a peptide linker which allows the two domains to associate to form an antigen binding site; (viii) bispecific single chain Fv dimers (WO 93/11161) and (ix) "diabodies", multivalent or multispecific fragments constructed by gene fusion (WO94/13804; 58). Fv, scFv or diabody molecules may be stabilised by the incorporation of disulphide bridges linking the VH and VL domains. Minibodies comprising a scFv joined to a CH3 domain may also be made.

In relation to a an antibody molecule, the term "selectively binds" may be used herein to refer to the situation in which one member of a specific binding pair will not show any significant binding to molecules other than its specific binding partner(s). The term is also applicable where e.g. an antigen-binding site is specific for a particular epitope that is carried by a number of antigens, in which case the specific binding member carrying the antigen-binding site will be able to bind to the various antigens carrying the epitope.

Pharmaceutical Compositions and Therapy

The active agents disclosed herein for the treatment of cancer may be administered alone, but it is generally preferable to provide them in pharmaceutical compositions that additionally comprise with one or more pharmaceutically acceptable carriers, adjuvants, excipients, diluents, fillers, buffers, stabilisers, preservatives, lubricants, or other materials well known to those skilled in the art and optionally other therapeutic or prophylactic agents. Examples of components of pharmaceutical compositions are provided in Remington's Pharmaceutical Sciences, 20th Edition, 2000, pub. Lippincott, Williams & Wilkins.

The term "pharmaceutically acceptable" as used herein includes compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The active agents disclosed herein for the treatment of cancer according to the present invention are preferably for administration to an individual in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

The formulations may conveniently be presented in unit dosage form and may be prepared by any methods well known in the art of pharmacy. Such methods include the step of bringing the active compound into association with a carrier, which may constitute one or more accessory ingredients. In general, the formulations are prepared by uniformly and intimately bringing into association the active compound with liquid carriers or finely divided solid carriers or both, and then if necessary shaping the product.

The agents disclosed herein for the treatment of cancer may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 mg/ml, for example from about 10 ng/ml to about 1 mg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Compositions comprising agents disclosed herein for the treatment of cancer may be used in the methods described herein in combination with standard chemotherapeutic regimes or in conjunction with radiotherapy. Examples of other chemotherapeutic agents include Amsacrine (Amsidine), Bleomycin, Busulfan, Capecitabine (Xeloda), Carboplatin, Carmustine (BCNU), Chlorambucil (Leukeran), Cisplatin, Cladribine (Leustat), Clofarabine (Evoltra), Crisantaspase (Erwinase), Cyclophosphamide, Cytarabine (ARA-C), Dacarbazine (DTIC), Dactinomycin (Actinomycin D), Daunorubicin, Docetaxel (Taxotere), Doxorubicin, Epirubicin, Etoposide (Vepesid, VP-16), Fludarabine (Fludara), Fluorouracil (5-FU), Gemcitabine (Gemzar), Hydroxyurea (Hydroxycarbamide, Hydrea), Idarubicin (Zavedos). Ifosfamide (Mitoxana), Irinotecan (CPT-11, Campto), Leucovorin (folinic acid), Liposomal doxorubicin (Caelyx, Myocet), Liposomal daunorubicin (DaunoXome®) Lomustine, Melphalan, Mercaptopurine, Mesna, Methotrexate, Mitomycin, Mitoxantrone, Oxaliplatin (Eloxatin), Paclitaxel (Taxol), Pemetrexed (Alimta), Pentostatin (Nipent), Procarbazine, Raltitrexed (Tomudex®), Streptozocin (Zanosar®), Tegafur-uracil (Uftoral), Temozolomide (Temodal), Teniposide (Vumon), Thiotepa, Tioguanine (6-TG) (Lanvis), Topotecan (Hycamtin), Treosulfan, Vinblastine (Velbe), Vincristine (Oncovin), Vindesine (Eldisine) and Vinorelbine (Navelbine).

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 mg to about 250 mg per kilogram body weight of the subject per day. Where the active compound is a salt, an ester, prodrug, or the like, the amount administered is calculated on the basis of the parent compound, and so the actual weight to be used is increased proportionately.

In combination therapy envisaged by the present invention the two active agents (or compositions comprising them) may be administered at the same time or spaced apart in time and/or site of administration. In some cases, the time between administration of the first of the two active agents and administration of the second of the two active agents may be between 1 minute and 1 week, e.g., between 5 minutes and 1 day, or between 5-60 minutes. Repeat doses of the respective inhibitors may be the same or different.

Generally, the dosing pattern of each of the two active agents will be dictated by the pharmacokinetics and pharmacodynamics of the respective agents in the subject to be treated. Thus, where one agent is metabolised or cleared more quickly than the other, it may require more frequent dosing in order to maintain effective combination therapy.

Determining MDSC IL-23 Secretion and/or Expression in the Tumor Microenvironment or Blood/Plasma As described in detail in the Examples herein, the present inventors have found that IL-23 secreted by myeloid-derived suppressor cells (MDSCs) confer castration resistance to prostate cancer cells. In particular embodiments, determining protein expression and/or level (e.g. IL-23 protein) comprises one or more of: determining protein expression in a tumour sample or blood or plasma sample using immunohistochemistry, immunofluorescence, measuring protein levels in a cell lysate or blood/plasma extract by ELISA or Western blotting, and/or using a binding agent capable of specifically binding to the IL-23 or subunit thereof (e.g. the p19 subunit), or a fragment thereof.

In certain cases, determining the expression of the gene of interest (e.g. the IL-23 gene) comprises extracting RNA from a sample of MDSCs in the tumor microenvironment and measuring expression by real time PCR and/or by using a probe capable of hybridising to RNA encoding the protein (e.g. IL-23), or a fragment thereof. Quantitative RT-PCR may employ primers having the sequences described in the Example, particularly the IL23p19 forward and reverse primers of SEQ ID NO: 13 and 14, respectively.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention. For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps. It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

The following is presented by way of example and is not to be construed as a limitation to the scope of the claims.

EXAMPLES

Materials and Methods

Animals

All mice were maintained under specific pathogen-free conditions in the IRB facility and experiments were performed according to state guidelines and approved by the local ethics committee. Male C57BL/6 or FVB mice 6-8 weeks of age were purchased from Jackson Laboratories (Envigo), and acclimated for at least a week before use. C57BL/6 IL-23p19KO (IL23ko) mice [20] were kindly provided by Prof. Federica Sallusto (IRB, Bellinzona). Pten$^{pc-/-}$ mice were generated and genotyped as previously described [17]. Female Pten$^{loxP/loxP}$ mice were crossed with male PB-Cre4 transgenic mice and genotyped for Cre using following primers: primer 1 (5'-AAAAGTTCCCCTGCTGATGATTTGT-3') and primer 2 (5'-TGTTTTTGACCAATTAAAGTAGGCTGTG-3') for PTEN$^{loxP/loxP}$; primer 1 (5' TGATGGACATGTTCAGGGATC 3') and primer 2 (5'CAGCCACCAGCTTGCATGA 3') for Probasin-CRE. Surgical castration was performed under anesthesia with isoflurane. Mice were monitored postoperatively for recovery from anesthesia and checked daily for 2 days postoperatively. Surgical skin clips were removed on postoperative day 5. Mice undergoing treatment were administered control vehicle or therapeutic doses of the appropriate agents. Any mouse suffering distress or greater than 15% weight loss during treatment was euthanized by $CO_2$ asphyxiation. At the completion of study, mice were euthanized by CO2 asphyxiation and tissue was collected for histology, mRNA analysis, protein analysis, and single cell suspensions for flow cytometry. For allograft experiments, $2.5 \times 10^6$ TRAMP-C1 cells, $2.5 \times 10^6$ TRAMP-C1 IL23RKO, or $2 \times 10^6$ MyC-CaP cells were injected subcutaneously into the flank of male respectively C57BL/6 or FVB mice. When tumors were approximately 100 mm$^3$, mice were randomized to the treatment groups. Tumor growth was monitored daily by measuring the tumor size with caliper. The tumor volume was estimated by calculating R1*R2*R3*4/3π, where R1 and R2 are the longitudinal and lateral radii, and R3 is the thickness of tumor protruding from the surface of normal skin. Animals were sacrificed when the tumor reached approximately 600 mm$^3$.

Treatments

αCXCR2 (AZD5069; AstraZeneca) was administered with daily intraperitoneal injections at a final concentration of 100 mg/kg on a Monday through Friday schedule. Control animals received vehicle. Enzalutamide (APExBio) was administered daily by oral gavage with a dose of 30 mg/kg/day on a Monday through Friday schedule. Rat anti-IL23 antibody (100 ng per mouse; G23-8; IgG1, kappa; eBioscience) or rat IgG1 isotype control (eBioscience) were administered weekly via intraperitoneal injection.

Bone Marrow Reconstitution

Bone marrow was flushed from the femors of male C57BL/6 or IL23p19ko mice under sterile conditions with RPMI 1640 using a 21-gauge needle. Mononuclear cells were filtered, collected and checked for viability using trypan blue. Before transplantation, bone marrow derived cells were depleted of CD3$^+$ T cells, NK1.1$^+$ NK cells and CD19$^+$ B cells by magnetic bead separation (STEMCELL Technologies). Recipient C57BL/6 or Pten$^{pc-/-}$ mice were lethally irradiated (900 rad) and transplanted i.v. two hours after with 1×10$^7$ viable bone marrow cells from either C57/BL6 or IL23p19ko mice.

Magnetic Resonance Imaging

Magnetic Resonance Imaging (MRI) was performed on castrated-Pten$^{pc-/-}$ mice 0, 4, 8, 12 and 16 weeks after surgical castration or on CTX IL23wt and CTX IL23ko Pten$^{pc-/-}$ mice 4, 8, 12 and 16 weeks after surgical castration using a 7T preclinical magnetic resonance scanner (Bruker, BioSpec 70/30 USR, Paravision 5.1), equipped with 450/675 mT/m gradients (slew-rate: 3400-4500 T/m/s; rise-time 140 µs) and a mouse body volume coil. Mice were under general anesthesia by 1.5-2% isoflurane vaporized in 100% oxygen (flow: 1 L/min).

Breathing and body temperature were monitored (SA Instruments, Inc., Stony Brook, N.Y., USA) and maintained around 30 breaths-per-minute and 37° C., respectively. MRI studies included a Rapid Acquisition with Relaxation Enhancement (RARE) High-Resolution T2-weighted (T2w) sequence with fat suppression acquired in the axial plane (TR=3800 ms, TE=45 ms, FOV=27 mm×18 mm, spatial resolution=0.094×0.087 mm/pixel, scan time=8 min, thickness 0.70 mm, 26 slices) and in the coronal plane (TR=3500 ms, TE=38 ms, FOV=33 mm×33 mm, spatial resolution=0.129×0.129 mm/pixel, scan time=5 min, thickness 0.60 mm, 20 slices). Images were analyzed using NIH software MIPAV (version 7.4.0). Circumference of the whole prostate was outlined on each RARE T2w axial slice containing identifiable prostate and the number of bounded pixels in each slice was computed and added to yield the prostate volume. Coronal T2w images were used for an accurate identification of the basal and apical limits of the prostate.

Differentiation of MDSCs in Vitro

Murine MDSCs were differentiated in vitro as previously described [25]. Briefly, bone marrow precursors were flushed from the femors of C57/BL6 or IL23p19ko mice with RPMI 1640 medium. The cell pellet was resuspended (one femor in 10 ml) in RPMI 1640 containing 10% heat-inactivated FBS, and the cells were cultured in vitro in the presence of 40 ng/ml GM-CSF and 40 ng/ml IL-6. On day 4, the cells were washed and resuspended with RPMI 1640 containing 10% heat-inactivated Charcoal Stripped-FBS. The day after the cells were stimulated with PMA/ionomycin and after 4 hours the supernatant was collected and stored at −80° C. Analysis of soluble molecules was conducted with Mouse CytokineMAP B version 1.0 by Rules Based Medicine (Austin, Tex.).

Human MDSCs were differentiated in vitro seeding 10$^6$/ml bone marrow precursors in T25 flasks with RPMI 1640 containing 10% heat-inactivated FBS in the presence of 10 ng/ml GM-CSF and 10 ng/ml IL-6 for 7 days [26]. Complete medium was changed when required. After 7 days, the cells were analyzed by flow cytometry for CD11b, CD33, CD15, HLA-DR expression and when the population CD11b$^+$, CD33$^+$, CD15$^+$, HLA-DR$^{neg}$ was higher than 80% the cells resuspended in RPMI 1640 containing 10% heat-inactivated Charcoal Stripped-FBS and after one day stimulated with PMA/ionomycin for 5 hours. The supernatant was then collected and stored at −80° C.

In Vitro Co-Culture Experiments

Prostate cancer cell lines were starved in Charcoal Stripped FBS (CS-FBS) medium for 72 h and then cultured with RPMI 1640 containing 10% heat-inactivated FBS (normal medium) or kept in full androgen deprivation medium (RPMI 1640 containing 10% heat-inactivated Charcoal Stripped-FBS plus Enzalutamide 10 µM; F.A.D.). Then, the cells were stimulated with or without condition media obtained from activated BM-derived MDSCs, or recombinant IL23 (100 ng/ml; R&D System), with or without αRORγ (5 µM; SR2211; Calbiochem®). Then, the cells were analyzed for Crystal Violet assay or stained with Annexin V/7AAD or collected for RNA extraction.

Analyses of IL23 and IL23R mRNA expression in clinical tumors HSPC RNA seq data for 550 patients was downloaded from the UCSC Cancer Browser (https://genome-cancer.ucsc.edu/proj/site/hgHeatmap/). mCRPC RNA seq data for 122 mCRPC patients was generated as part of SU2C effort [27]. The paired-end transcriptome sequencing reads were aligned to the human reference genome (GRCh37/hg19) using Tophat2 [28] (Tophat 2.1.0). Gene expression, as fragments per kilobase of exon per million fragments mapped (FPKM; normalized measure of gene expression), was calculated using Cufflinks [29]. MDSC marker (CD11b, CD33, CD14 and CD15) positive and negative was defined by the high quantiles and low quantiles RNA expression of each transcript and IL23/IL23R expression level in each biomarker groups were compared by student t test. In order to compare gene expression level between TCGA and SU2C with minimum experimental bias, we only included genes expressed in both TCGA and SU2C with median expression level (FPKM)>>0. The gene expression levels in each sample were quantile normalized, and IL23 expression levels in HSPC and CRPC were compared using t test.

Human Organoids

Organoids were grown in 3D Matrigel® (cat.356231, Corning) under prostate epithelial conditions [30]. Cell viability was measured using 3D CellTiter-Glo® 3D reagent (cat.G9681, Promega) by quantifying metabolically active cells releasing ATP. Cell line-derived organoids were plated at a density of 2000 cells per well in 96-well optical plates (cat.3610, Corning) embedded in Matrigel® as hanging drops (5 µl per well). Cells were treated with recombinant IL23 (cat 300-01A, PeproTech) at 100 ng/ml or culture with Enzalutamide (10 uM) with or without recombinant IL23. The luminescence measurement was performed after 7 days in culture. Each IL23 condition was normalized for its experimental control.

Immune Tumor Microenvironment Characterization

Tumors were disaggregated and digested in collagenase D and DNAse for 30 minutes at 37° C. to obtain single-cell suspension. For intracellular cytokine detection cells where stimulated for 5 hours with PMA/ionomycin. After neutralization of unspecific binding with αCD16/CD32 (clone 93), single-cell suspensions were stained with specific mAb (primary antibodies directly conjugated) to assess the phenotype. The antibodies used were: αCD45 (clone 30-F11); αLy-6G (clone 1A8); αLy6C (clone HK1.4), αCD11b (clone M1/70); αF4/80 (clone BM8), αCD206 (clone C068C2), αCD11c (clone N418), αB220 (clone RA3-6B2), αCD3 (clone 145-2C11), αCD8 (clone 53-6.7), αCD4 (clone GK1.5), αNK1.1 (clone PK136), αCD90.2 (clone 30-H12), αPDL1 (clone 10F.9G2), αEpCAM (clone G8.8), αIL17 (clone TC11-18H10.1), αIL23p19 (clone FC23CPG), αIL23R (clone 12B2B64). All the antibodies were purchased from eBioscience or Biolegend. Samples were acquired on a BD Fortessa flow cytometer (BD Biosciences). Data were analyzed using FlowJo software (TreeStar, Ashland, Oreg.).

Immunohistochemistry and Immunofluorescence

For immunohistochemistry (IHC), tissues were fixed in 10% formalin (ThermoScientific, 5701) and embedded in paraffin in accordance with standard procedures. Preceding immunohistochemical staining, tumor sections (4 µm) were exposed to two washes with OTTIX plus solution (Diapath, X0076) and subsequent hydration with OTTIX shaper solution (Diapath, X0096) followed by deionized water. Antigen unmasking was performed by heating sections in the respective pH solutions based on the antibodies used at 98° C. for 20 minutes. Subsequently the sections were blocked for peroxidases and nonspecific binding of antibodies using 3% $H_2O_2$ (VWR chemicals, 23615.248) and Protein-Block solution (DAKO Agilent technologies, X0909) respectively for 10 mins each split by 0.5% PBST washing. H&E staining was performed according to standard procedures. Sections were stained for anti-Ki67 (Clone SP6; Lab Vision Corporation), anti-pSTAT3 (TYR705; clone D3A7; Cell Signaling), anti-CD3 (cod.A0452; DAKO). Images were obtained using objectives of 5×, 10×, 40× magnification and Pixel image of 1.12 µm and 0.28 µm respectively. All the quantifications have been done using the public online software ImmunoRatio (153.1.200.58:8080/iimunoratio/). For the immunofluorescence (IF) staining, tissue paraffin embedded sections were stained for 4',6-Diamidine-2'-phenylindole dihydrochloride (DAPI) (#70238421, Roche), anti-IL23 (ab45420; Abcam), anti-Ly6G (RB6-8C5; GeneTex). Confocal images were obtained with the Leica TCS SP5 confocal microscope using×10/1.25 oil.

In Vitro T Cell Suppression Assay

In vitro suppression assays were carried out in RPMI/10% FCS in 96-well U-bottom plates (Corning, N.Y.). Naive splenocytes were labeled with 5 µM CFSE (Molecular Probes) and activated in vitro with anti-CD3 and anti-CD28 beads (Invitrogen) according to the manufacturer's instructions. Conditioned media of BM-MDSCs was added to the culture. After 3 days, the proliferation of CFSE-labelled $CD8^-$ T cells was analyzed by BDFortessa.

CRISPR-Cas9 Transfection

TRAMP-C1 cells were grown in 75 $cm^2$ flask to a 50-60% confluence in DMEM medium supplemented with 10% heat-inactivated FBS, 100 U/ml penicillin, 0.1 mg/ml streptomycin and 2 mM L-glutamine. The transfection of the IL23R CRISPR/Cas9 KO plasmid (Santa Cruz Biotechnology) was performed using jetPRIME® transfection reagent according to the manufacturer's protocol at the 1:2 DNA/jetPRIME® ratio. 24 h after transfection, the GFP transduced cells were sorted to purity 99% and plated as single cell on 96-well plates. At day 7 after cell sorting the grown cell colonies were moved into 24-well plates for further expansion. The knock-down of IL23R gene in each cell colony was confirmed by Western blot.

NanoString

The nCounter analysis system (NanoString Technologies, Seattle, Wash.) was used to screen for the expression of signature genes associated with cancer-inflammation pathway. Two specific probes (capture and reporter) for each gene of interest were employed. Briefly, 5 µl of RNA (the concentration is higher than 25 ng/µl) was hybridized with customized Reporter CodeSet and Capture ProbeSet as Mouse PanCancer Immune Profiling Panel including 700 selected genes (NanoString Technologies) according to the manufacturer's instructions for direct labeling of mRNAs of interest with molecular barcodes without the use of reverse transcription or amplification. Total RNA was quantified by NanoDrop ND-1000 Spectrophotometer (NanoDrop Technologies, Wilmington, Del.) and RNA quality was assessed using Agilent 2100 bioanalyzer (Agilent Technologies, Santa Clara, Calif.). The hybridized samples were then recovered in the NanoString Prep Station and the mRNA molecules were counted with the NanoString nCounter. For analysis of expression, each sample profile was normalized to geometric mean of 20 housekeeping genes included in the panel.

Multiplex Immunofluorescence (IF) in Formalin Fixed Paraffin Embedded Human Tissue Section Multiplex immunofluorescence for CD15 (#M3631, Dako, clone Carb-3), CD33 (#ab11032, Abcam, clone 6C5/2), CD11b (#ab52477, Abcam, clone EP1345Y) and EpCAM Alexa Fluor® 647 conjugate (#5447S, Cell Signaling, clone VU1D9) was performed using 4 µm sections of formalin fixed paraffin embedded prostate tumor samples by sequential staining after antigen retrieval in CC1 (pH 8.5) (#950-224, Ventana) in water bath at 98° C. for 36 minutes. First, mouse monoclonal (IgG1) antibody anti-CD33 (1:100 dilution), mouse monoclonal (IgM) anti-CD15 (1:200 dilution) and rabbit monoclonal (IgG) antibody anti-CD11b (1:100 dilution) were incubated for one hour after blocking with 10% goat serum for 30 minutes. Primary antibodies were detected with goat anti-mouse IgG1 Alexa Fluor® 555-conjugated (Life Technologies, 1:200 dilution), goat anti-mouse IgM Alexa Fluor® 488-conjugated (Life Technologies, 1:200 dilution) and goat anti-rabbit IgG (H+L) Alexa Fluor® 700-conjugated (Life Technologies, 1:200 dilution) antibodies for 30 minutes. Next, tissue sections were treated with 5% mouse/rabbit normal serum for 30 minutes, followed by incubation with mouse monoclonal (IgG1) anti EpCAM antibody conjugated to Alexa Fluor® 647 (dilution, 1:200) for one hour. The samples were washed three times for 5 minutes with TBS-Tween 0.05% between incubations. Nuclei were counterstained with DAPI (#70238421, Roche) and tissue sections were mounted with ProLong Gold antifade reagent (#P36930, Molecular Probes). Slides were imaged with a multispectral fluorescence microscope (Vectra v2.0.8, PerkinElmer) under ×20 magnification.

After staining, slides were scanned using the multi-spectral camera provided by Vectra®(Perkin Elmer) system. The number of images collected per case was dependent on tumor size (Min.=1, Max.=14, Average=5). Quantification of PMN-MDSC like cells ($CD15^+$ $CD33^+$ $CD11b^+$) was performed using inForm v2.1.1 software (PerkinElmer) and the density of cells of interest are presented as number of cells per mm². Tissue segmentation algorithm based on EpCAM positivity was used to separate tumor from adjacent stroma. The algorithm was trained to perform cell segmentation using counterstain based segmentation achieved with nuclear DAPI staining. Phenotype determination was based on positivity for CD15, CD33 and CD11b. Cells in tumor areas selected by the algorithm were then separated into bins as follows: CD15+ CD33+ CD11b+ were called PMN-MDSCs. All tissue segmentations, cell segmentation and phenotype determination maps were reviewed by a pathologist.

RNA Expression/Quantitative Real-Time PCR

RNA isolation (TRIzol, Qiagen) and retro-transcription with SuperScriptIII (Invitrogen, 11752-250) were performed according to the manufacturer's instructions. Quantitative PCR (qPCR) reactions (Bio-Rad) were performed using KAPA SYBR FAST qPCR green (KK4605; Applied Biosystems) and the specific primers reported below. Primer sequences were obtained from PrimerBank (http://pga.mgh.harvard.edu/primerbank/index.html) or BIORAD. Each expression value was normalized by HPRT or GADPH level as reference.

```
The primer sequences used were as follows:
GranzymeB forward
                                          (SEQ ID NO: 1)
5'-CCACTCTCGACCCTACATGG-3', reverse
                                          (SEQ ID NO: 2)
5'-GGCCCCCAAAGTGACATTTATT-3';

IFNγ forward
                                          (SEQ ID NO: 3)
5'-GCTCTGAGACAATGAACGCT-3', reverse
                                          (SEQ ID NO: 4)
5'-AAAGAGATAATCTGGCTCT-3';

TNFα forward
                                          (SEQ ID NO: 5)
5'-CCTGTAGCCCACGTCGTAG-3', reverse
                                          (SEQ ID NO: 6)
5'-GGGAGTAGACAAGGTACAACCC-3';

IL-10 forward
                                          (SEQ ID NO: 7)
5'-GCTCTTACTGACTGGCATGAG-3', reverse
                                          (SEQ ID NO: 8)
5'-CGCAGCTCTAGGAGCATGTG-3';

TGFb forward,
                                          (SEQ ID NO: 9)
5f-CTCCCGTGGCTTCTAGTGC-3';

reverse,
                                          (SEQ ID NO: 10)
5'-GCCTTAGTTTGGACAGGATCTG-3';

GADPH forward,
                                          (SEQ ID NO: 11)
5'-AGGTCGGTGTGAACGGATTTG-3';

reverse,
                                          (SEQ ID NO: 12)
5'-TGTAGACCATGTAGTTGAGGT-3';

IL23p19 forward,
                                          (SEQ ID NO: 13)
5f-CCAGCAGCTCTCTCGGAATC-3';

reverse,
                                          (SEQ ID NO: 14)
5'-TCATATGTCCCGCTGGTGC-3'.
```

BIORAD primers used were: HPRTPrimePCR™ PreAmp for SYBR® Green Assay: Hprt, Mouse qMmuCID0005679; AR PrimePCR™ PreAmp for SYBR® Green Assay: Ar, Mouse BIORAD qMmuCID0005164; NKX3.1PrimePCR™ PreAmp for SYBR® Green Assay: Nkx3-1, Mouse qMmuCED0046482; PBSNPrimePCR™ PreAmp for SYBR® Green Assay: Pbsn, Mouse qMmuCID0017831; FKBPSPrimePCR™ PreAmp for SYBR® Green Assay: Fkbp5, Mouse qMmuCID0023283.

Western Blot Analyses and Protein Detection

Tissue and cell lysates were prepared with RIPA buffer (1×PBS, 1% Nonidet P40, 0.5% sodium deoxycholate, 0.1% SDS and protease inhibitor cocktail; Roche). Total protein concentration was measured using BCA Protein Assay Kit (Cat: 23225; Pierce, Rockford). Equal amounts of proteins were separated by SDS-PAGE and Western blotted onto a 0.45 μm-nitrocellulose membrane. Membranes were blocked in 5% defatted milk or 5% BSA in Tris-buffered saline containing 0.1% Tween-20 (TBST), probed with diluted antibodies and incubated at 4° C. overnight. The following primary antibodies were utilized: rabbit polyclonal anti-HSP90 (1:1000 dilution, Cell Signaling), rabbit polyclonal anti-phospho-Stat3(Tyr705) (1:1000 dilution, Cell Signaling), rat monoclonal anti-RORγt (5:1000 dilution, clone AFKJS-9, eBioscience), rabbit polyclonal anti-IL23R (H-300) (1:1000 dilution, Santa Cruz). After washing in TBST, the membrane was incubated with secondary antibody conjugated with horseradish peroxidase (HRP) (dilution 1:5000, Cell Signaling). The protein bands were visualized using the ECL Western Blotting Substrate (Pierce).

Human Prostate Samples

All patient samples consenting to the trial were men with metastatic CRPC. These patients had at diagnosis a median age of 63 years and a median PSA of 94.7. All patients had received between 1-5 lines of therapy in the castration resistant setting at the time samples were taken (including docetaxel, cabazitaxel, enzalutamide, abiraterone and Radium 223). Archival hormone-sensitive tissue samples were collected from prostatic needle biopsies, transurethral resections of the prostate or prostatectomies. CRPC samples were taken from the primary tumor or more commonly from metastases (bone, lymph node or viscera). All tissue blocks were re-sectioned and reviewed by a pathologist who confirmed adequacy of the material. PTEN protein expression was determined by immunohistochemistry with H-scores being graded by a pathologist.

Statistical Analysis and Reproducibility

Data analyses used GraphPad Prism version 7. The data are presented as mean±standard error of the mean, individual values as scatter plot with column bar graphs and were analyzed using Student's t-tests (paired or unpaired according to the experimental setting) by a two-sided and, when indicated, followed by Wilcoxon posttest. One-way ANOVA was used to compare three or more groups in time point analyses. Differences were considered significant when P<0.05 and are indicated as NS, not significant, *P<0.05, P<0.01, *P<0.001. Non-parametric tests were applied when variables were not normally distributed using the SPSS statistical software. N values represent biological replicates. Survival curves were compared using the Log-rank test (Mantel-Cox). For statistical analyses of PMN-MDSCs in human tumor tissue a mixed effect negative binomial regression model was used including a per patient random intercept and adjusting for tumor area as an exposure variable (Coefficient: 1.12; 95% CI: 0.34 to 1.90; P=0.005). All the statistics and reproducibility are reported in the figure legend. For animal studies, sample size was defined on the basis of past experience with the models [12], to detect differences of 20% or greater between the groups (10% significance level and 80% power). For ethical reasons the minimum number of animals necessary to achieve the scientific objectives was used. Animals were allocated randomly to each treatment group. Different treatment groups were processed identically and animals in different treatment groups were exposed to the same environment.

Figure 5:
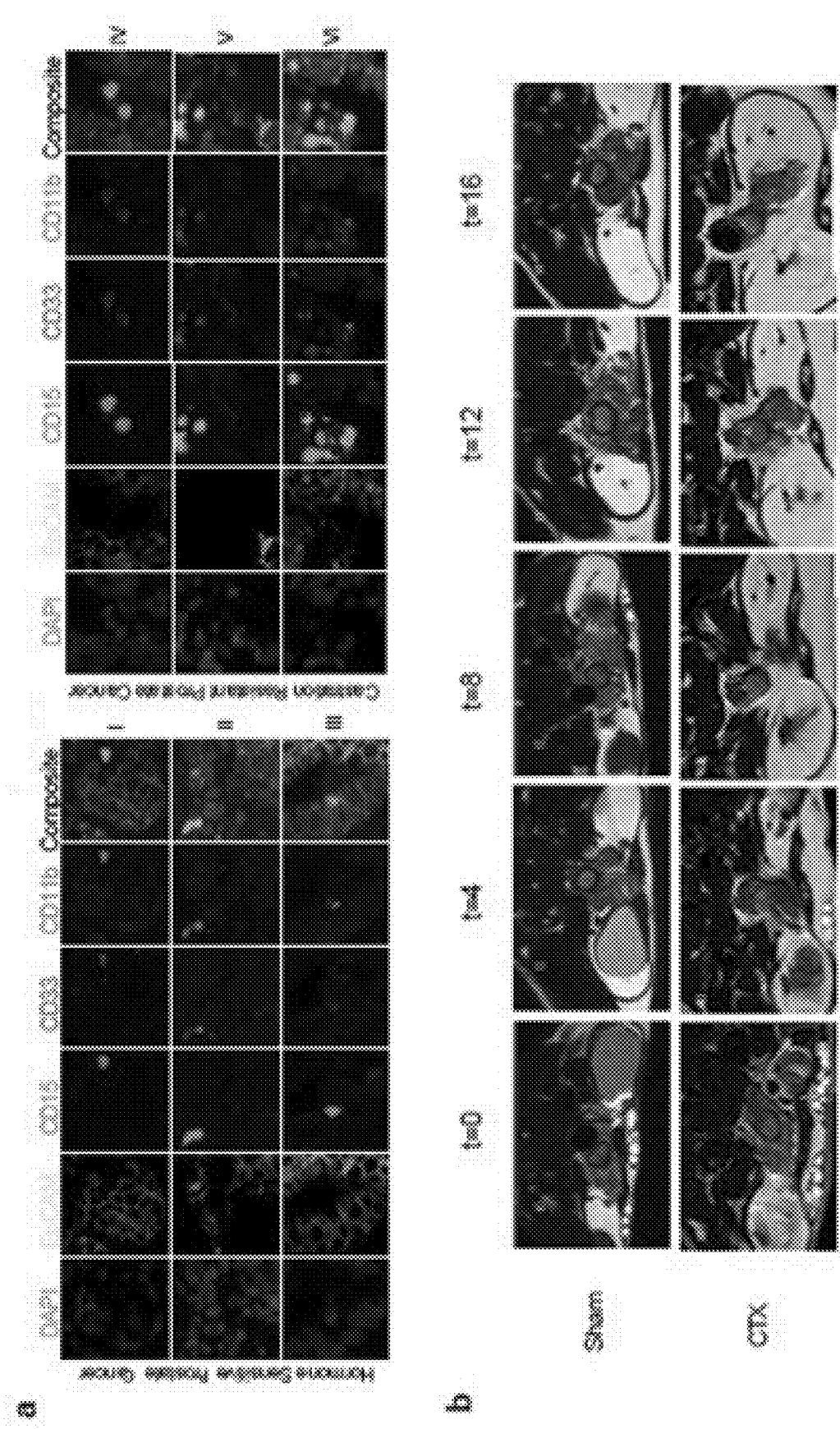
FIGS. 5A-5H. Multispectral images of PMN-MDSCs in human biopsies and set up of the different CRPC mouse models. a, Multispectral microscopy images (EpCAM yellow, CD15 green, CD33 red; CD11b pink) of hormone sensitive vs castration resistant prostate cancers. b, MRIs of representative Sham-operated (Sham) or surgical castrated (CTX) Pten$^{pc-/-}$ mice at different time points. c, Waterfall plot depicting proportional change in tumor response for Sham (n=3) and CTX (n=3) Pten$^{pc-/-}$ mice. Mean±SE. Statistical analyses (Unpaired Student t test): P<0.01; *P<0.001. d, Representative gating strategy of flow cytometry data in prostate of Sham-operated mouse. e, Schematic representation of the experiment. Six-week-old C57BL/6 males were challenged s.c. with TRAMP-C1 cells. When tumors reached≈100 mm3, mice were sham-operated (Sham, n=9) or surgically castrated (CTX, n=5). Average tumor volume (mean±SE) for each experimental group. Statistical analyses (Unpaired Student t test followed by Wilcoxon posttest): *P<0.05. f, Tumor PMNMDSCs frequencies determined by flow cytometry during CS and CR phase. Mean±SE. Each dot represents an individual mouse. Statistical analyses (Unpaired Student t test): *P<0.05; P<0.01; *P<0.001. g, Schematic representation of the experiment. Six-week-old FVB males were challenged s.c. with Myc-CaP cells. When tumors reached≈100 mm3, mice were sham-operated (Sham, n=3) or surgically castrated (CTX, n=3). Average tumor volume (±SE) for each experimental group. Statistical analyses (Unpaired Student t test followed by Wilcoxon posttest): *P<0.05. h, Tumor PMN-MDSCs frequencies determined by flow cytometry during CS and CR phase. Mean±SE. Each dot represents an individual mouse. Statistical analyses (Unpaired Student t test): **P<0.01.
Figure 5:
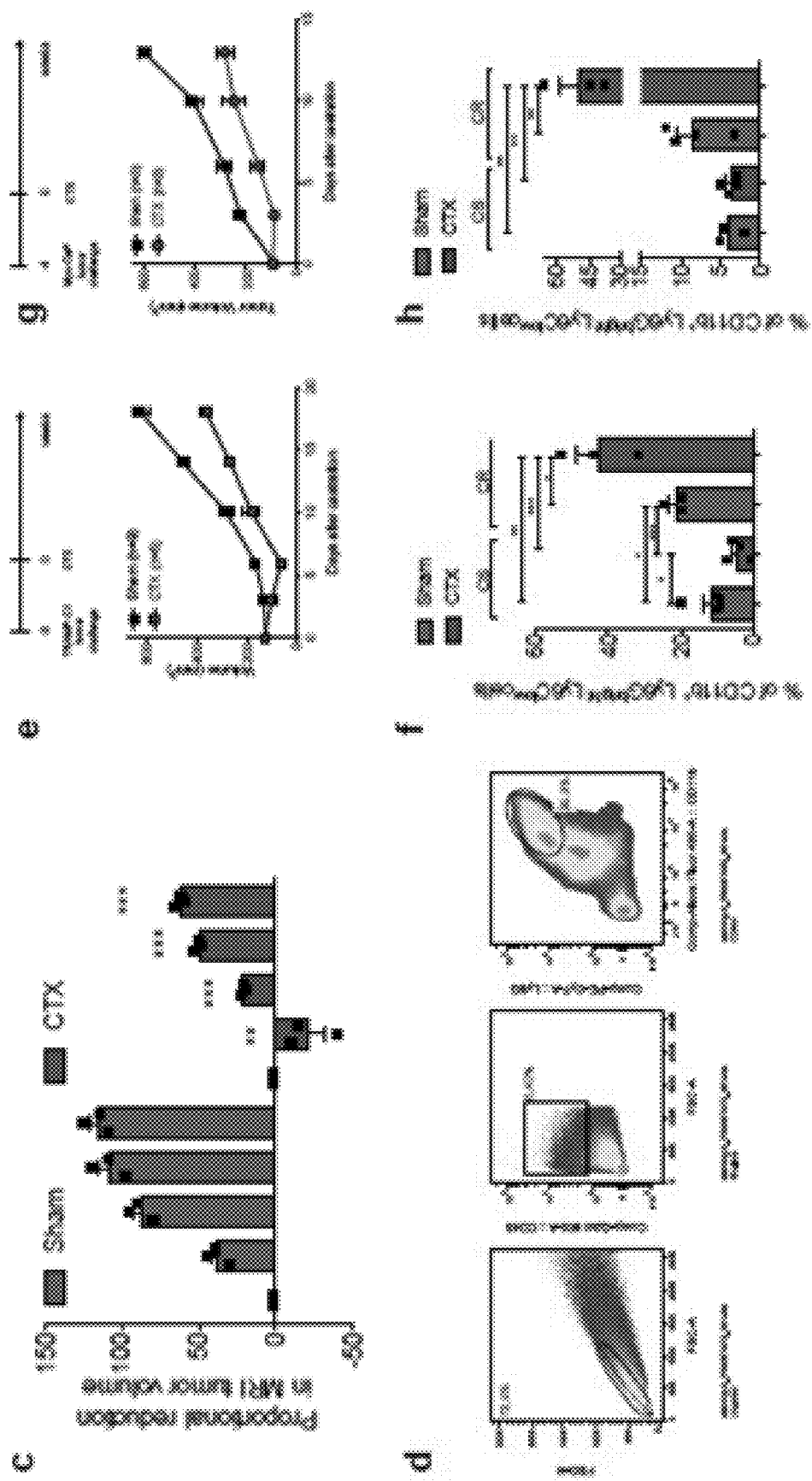
Figure 6:
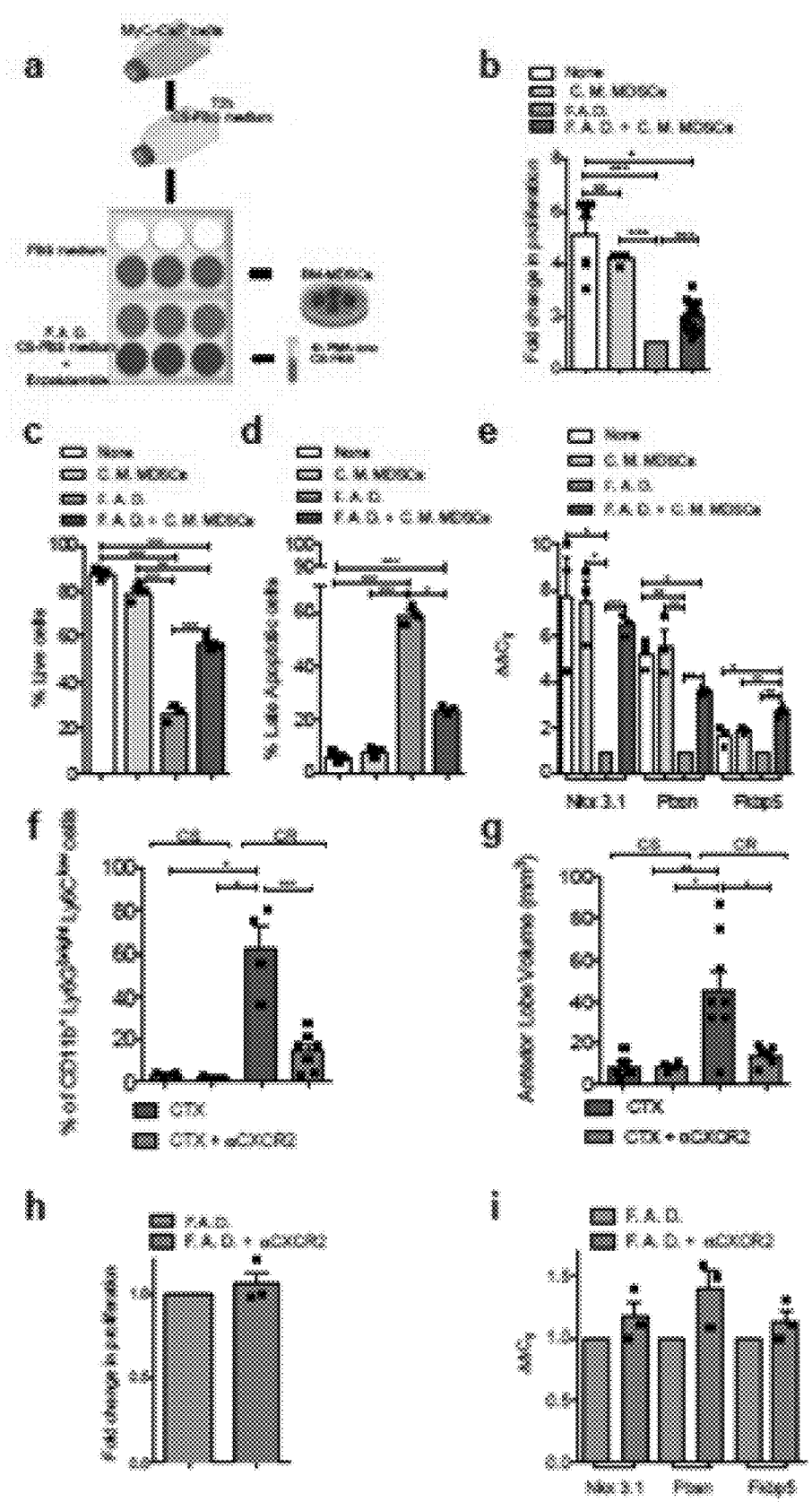
FIGS. 6A-6I. Factors secreted by MDSCs promote insensitivity to androgen deprivation in MyC-CaP prostate cancer cells and their impaired tumor recruitment enhances response to surgical castration in Pten$^{pc-/-}$ mice. a, Experimental scheme. Briefly, MyC-CaP prostate cancer cells were starved in Charcoal Stripped FBS (CS-FBS) for 72 h and then cultured with normal medium or kept in F.A.D., with or without C.M. MDSCs. b, Cell proliferation of MyC-CaP cells after 72 h of coculture (fold change compared with F.A.D. condition). c, Percentage of AnnexinV and 7AAD negative MyC-CaP cells. d, Percentage of AnnexinV-positive and 7AAD-negative MyC-CaP cells. e, qRT-PCR analyses of the indicated genes in MyC-CaP cells after 24 h of co-culture (fold change compared with F.A.D. condition).
Figure 7:
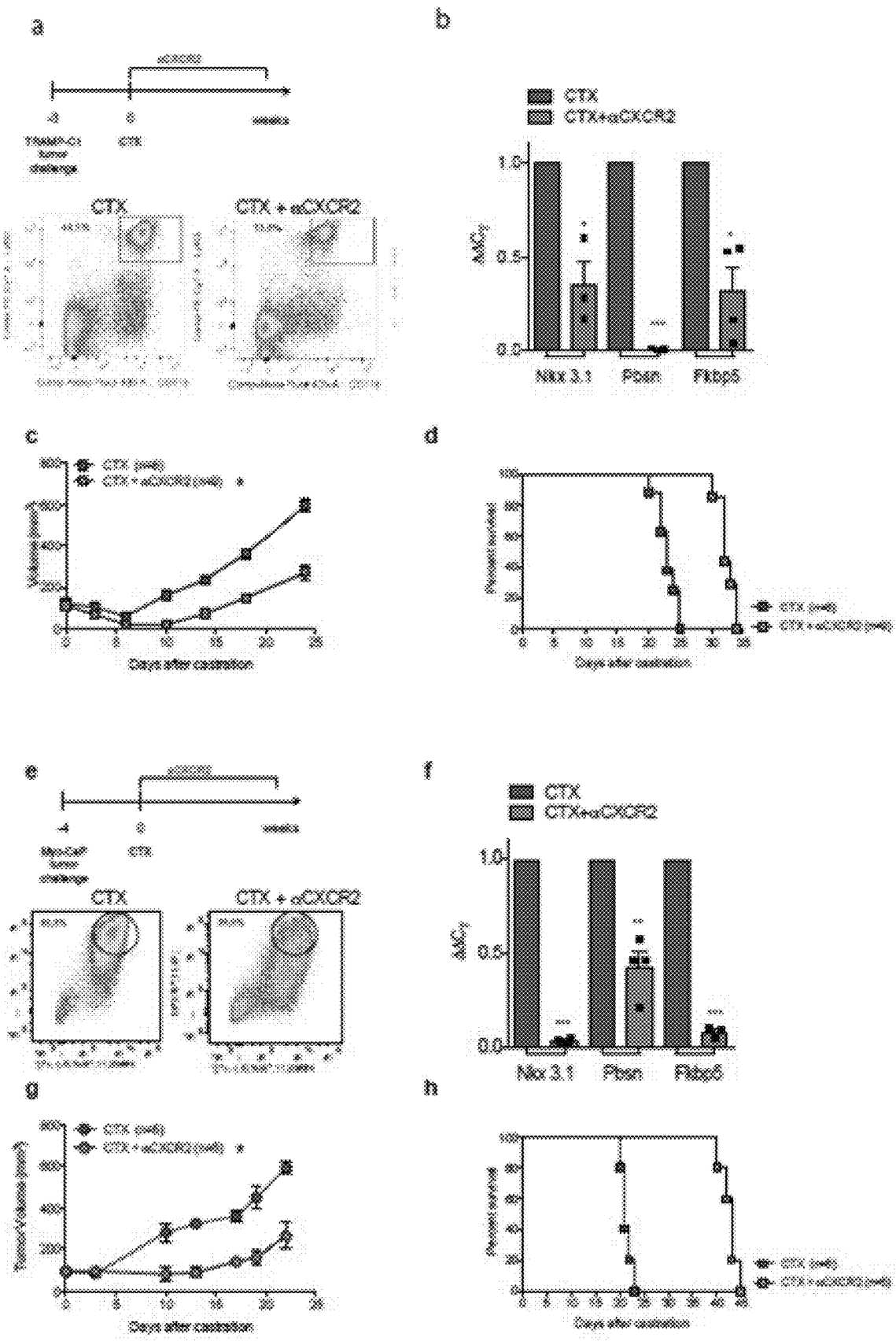

Example 1—IL23 Secreted by Myeloid-Derived Suppressor Cells Confers Castration Resistance in Prostate Cancer Increased numbers of circulating and tumor-infiltrating MDSCs have been observed in patients affected by different tumors including prostate cancer [8,9]. MDSCs are known to support tumorigenesis by either suppressing the antitumor immune response or by promoting angiogenesis and senescence evasion 10-12. By analyzing a cohort of hormone-sensitive (HSPC) and castration resistant prostate cancer (CRPC) patients we found that Polymorphonuclear (PMN)-MDSCs (CD11b$^+$ CD33$^+$ CD15$^+$ cells) [13] are enriched in the tumors of CRPC when compared to HSPC patients (FIG. 1a; FIG. 5a). Interestingly, these cells localize in close proximity of EpCAM$^+$ epithelial tumor cells (FIG. 1a; FIG. 5a). These findings prompted us to hypothesize that tumor infiltrating PMN-MDSCs could directly contribute to the emergence of CRPC. We investigated this hypothesis by using the Ptennull prostate conditional (Pten$^{pc-/-}$) mouse model and two additional allograft models of prostate cancer (TRAMP-C1 and MyC-CaP). As previously reported [14], surgical castration in Pten$^{pc-/-}$ mice leads to initial tumor regression (castration sensitive (CS) phase, (t=4)) followed by tumor progression and emergence of castration resistant prostate tumors (castration resistant (CR) phase (t=12)) (FIG. 1b; FIG. 5b-c), with AR target genes being down-regulated in the CS phase and up-regulated in the CR phase of the tumors when compared with sham-operated mice (FIG. 1c). To assess whether castration affects the recruitment of PMN-MDSCs in the tumors, we measured the abundance of PMNMDSCs (CD11b$^+$ Ly6G$^{bright}$ Ly6C$^{low}$ cells) [13] in sham-operated and castrated Pten$^{pc-/-}$ mice in a time course experiment (FIG. 1d). Interestingly, PMN-MDSCs number increased over time, paralleling the emergence of CRPC in mice (FIG. 1b, d; FIG. 5d). Of note, PMN-MDSCs represented the major immune subset that increased in Pten null tumors upon castration (FIG. 1e). This increase in PMN-MDSCs was validated in TRAMP-C1 and MyC-CaP castrated-models that develop CRPC within 10 days after castration (FIG. 5e-h). To assess whether factors secreted by MDSCs impact AR pathway in prostate tumor cells, we co-cultured two murine androgen-dependent prostate cancer cell lines, TRAMP-C1 and MyC-CaP, in the presence of conditioned medium (C.M.) obtained from bone marrow (BM)-derived MDSCs (FIG. 1f; FIG. 6a). Surprisingly, the C.M. of MDSCs sustained the proliferation and survival of cells cultured under full androgen deprivation (F.A.D.), enhancing the transcription of androgen receptor (F.A.D.), enhancing the transcription of androgen receptor target genes (FIG. 1g-j, FIG. 6b-e). These results were further validated in human LNCaP cells (androgen-dependent prostate cancer cell line cocultured in presence of C.M. from human MDSCs; FIG. 1k-l). Taken together, these data demonstrate that MDSCs regulate in a paracrine manner AR sensitivity in prostate tumor cells. We next assessed whether tumor depletion of MDSCs could delay the emergence of CRPC in castrated mice. We therefore treated castrated Pten$^{pc-/-}$ mice, TRAMP-C1, and MyC-CaP allografts mice with AZD5069, a selective CXCR2 antagonist (αCXCR2) under clinical evaluation [15]. Treatment with AZD5069 strongly reduced the tumor infiltration of PMN-MDSCs in all the mouse models analysed (FIG. 6f; FIG. 7a, e). Notably, while Pten$^{pc-/-}$ castrated mice treated with αCXCR2 did not progress to CRPCs, untreated mice developed CRPCs four months after castration as demonstrated by the levels of AR target genes (FIG. 6g; FIG. 1m). This finding was also confirmed in TRAMP-C1 and MyC-CaP allograft mice, where inhibition of MDSCs tumor recruitment delayed the emergence of CRPC as shown by decreased tumor size and level of AR target genes in treated mice, resulting in longer survival in AZD5069 treated mice (FIG. 7). Of note, αCXCR2 treatment did not directly affect cell proliferation and AR activity in mouse prostate tumor cells cultured in F.A.D., in vitro (FIG. 6h-i). Taken together, these data demonstrate that MDSCs are increased in human CRPC and promote prostate tumor cell proliferation by sustaining AR signaling in castrated mice.

Figure 2:
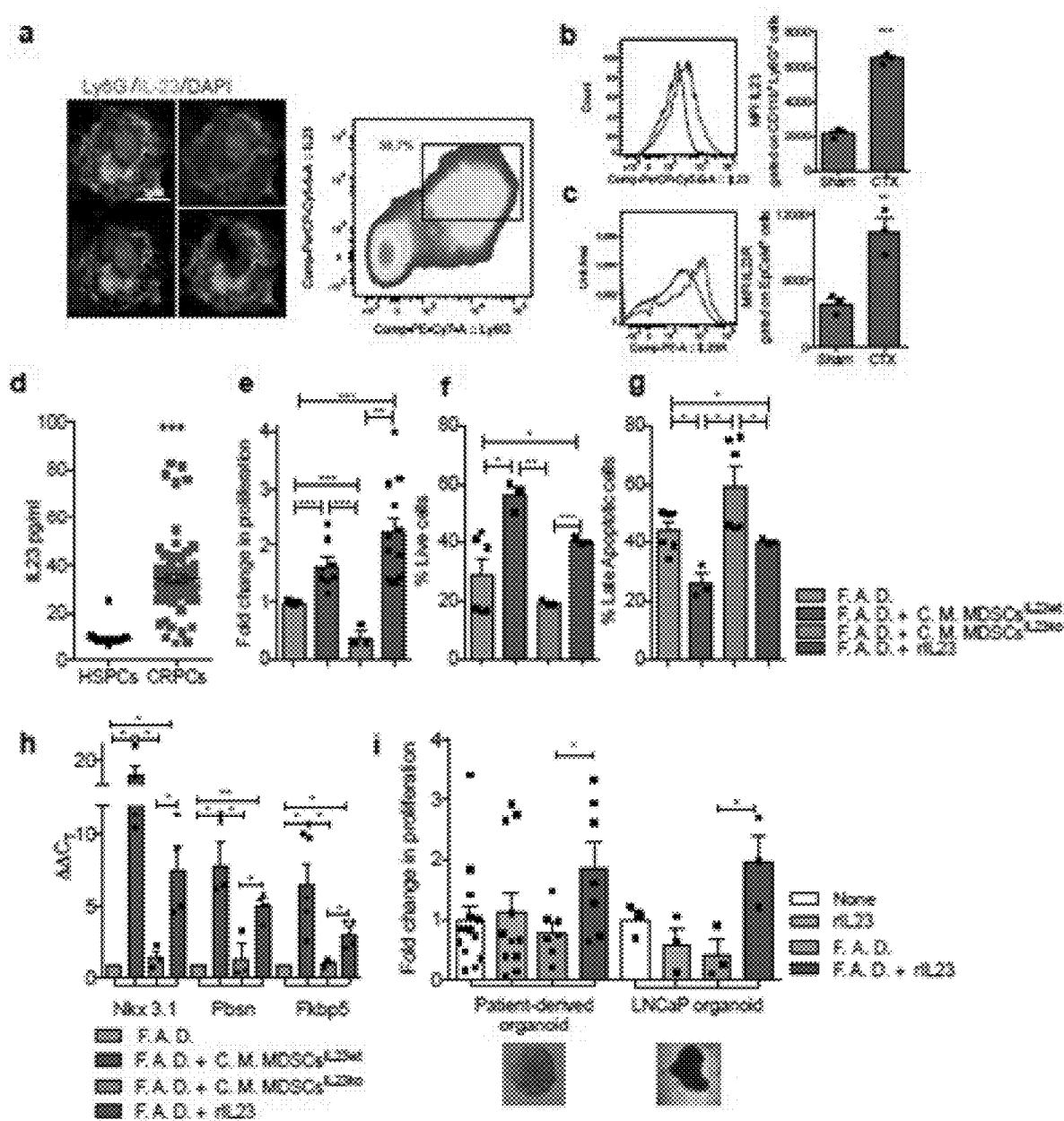
FIGS. 2A-2I. MDSC-derived IL23 drives insensitivity to androgen deprivation. a, Representative confocal images of $Ly6G^+$ (red) $IL23^+$ (green) cells in CTX $Pten^{pc-/-}$ mice prostate lesions (nuclei, blue (DAPI). Scale bar, 5 μm), and representative dot plot of $Ly6G^+$ $IL23^+$ cells gated on CD45+ cells within the prostate of CTX $Pten^{pc-/-}$ mice. b, Mean fluorescence intensity (MFI) of IL-23 within CD45+ $CD11b^+$ $Ly6G^+$ cells analyzed by flow cytometry in the prostate tumors of Sham and CTX $Pten^{pc-/-}$ mice (n=4 per group). Representative histograms (left panel) and quantification (right panel) is reported as mean±SE. c, Mean fluorescence intensity (MFI) of IL-23R gated on $CD45^-$ $EpCAM^+$ cells analysed by flow cytometry in the prostate tumors of sham and CTX $Pten^{pc-/-}$ mice (n=3 per group). Representative histograms (left panel) and quantification (right panel) is reported as mean±SE. d, IL23 levels in the plasma of hormone sensitive prostate cancer (HSPC; n=20) and castration resistance prostate cancer (CRPC; n=92) patients. Data are reported as mean±SE. e, f, g, h, TRAMP-C1 prostate cancer cells were starved as described in FIG. 1f and then kept in full androgen deprivation medium (F.A.D.), then cultured in presence of condition media obtained from IL23wt BM-derived MDSCs (C.M. $MDSCs^{IL23wt}$) or IL23ko BM-derived MDSCs (C.M. $MDSCs^{IL23ko}$) or recombinant IL23 (rIL23). e, Cell proliferation of TRAMP-C1 cells after 72 h of co-culture (fold change compared with F.A.D. condition). f, Percentage of AnnexinV and 7AAD negative TRAMP-C1 cells. g, Percentage of AnnexinV-positive and 7AAD-negative TRAMP-C1 cells. h, qRT-PCR analyses of the indicated genes in TRAMP-C1 cells after 24 h of co-culture (fold change compared with F.A.D. condition). e-h Aggregated data from five independent experiments are reported as mean±SE. Each dot represents a biological replicate. i, Cell proliferation of 3D culture of mCRPC patient derived organoid and LNCaP derived organoid cultured in normal medium or under F.A.D. with or without recombinant IL23. rIL23 conditions were normalized to the None or F.A.D. condition respectively. Aggregated data from three independent experiments are reported as mean±SE. Each dot represents a biological replicate. b-g, i, Statistical analyses (Unpaired Student t test): *P<0.05; P<0.01; *P<0.001. h, Statistical analyses (Paired Student t test between F.A.D. and the other group and Unpaired Student t test between all the others): *P<0.05; P<0.01; *P<0.001.
Figure 8:
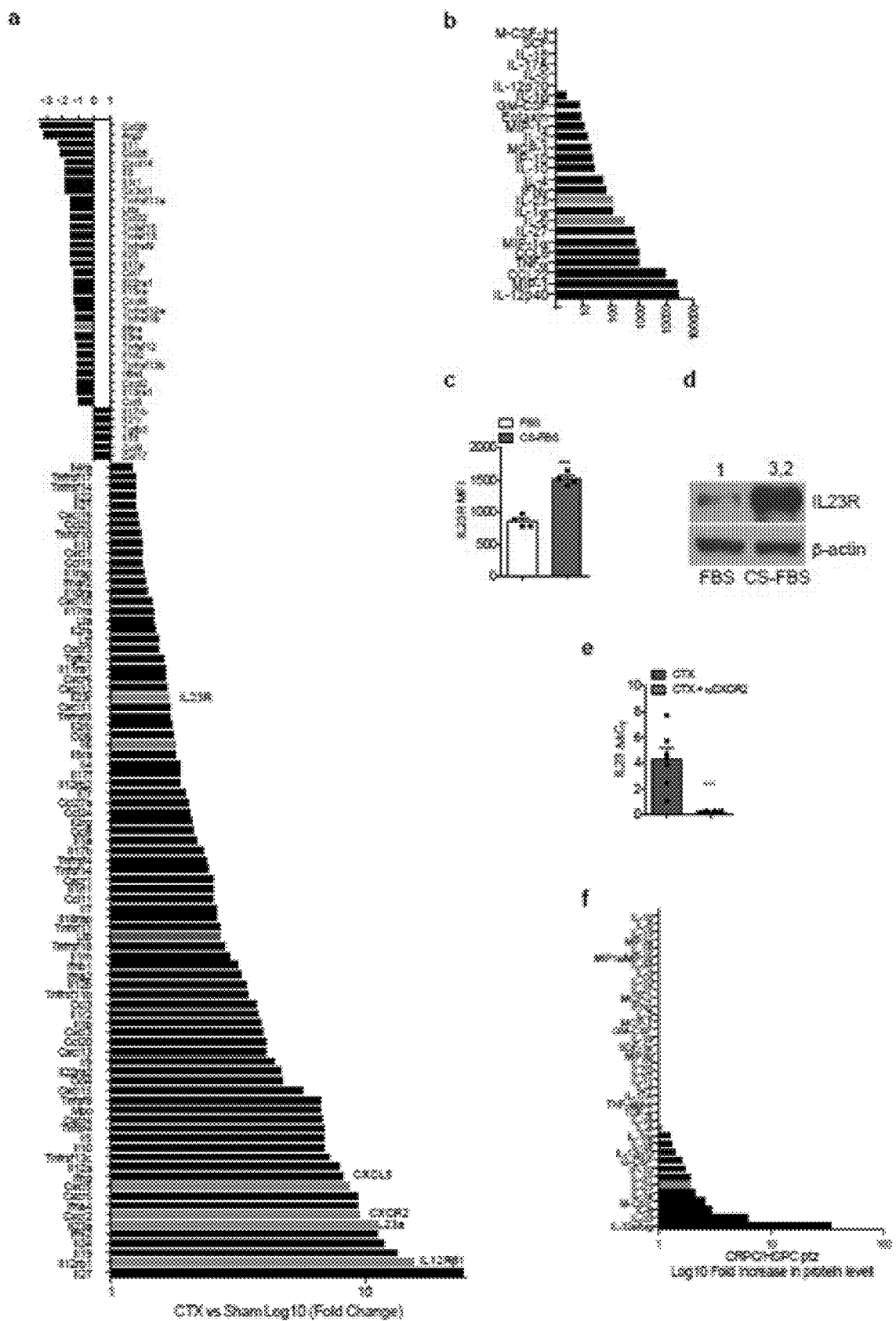

To identify factors secreted by MDSCs, which may drive castration resistance, we performed a NanoString nCounter gene expression assay in Pten$^{pc-/-}$ tumors from sham and castrated mice. IL23 and one of the subunits of IL23 receptor (IL12Rβ1) were the most up-regulated genes in castrated tumors when compared to controls (FIG. 8a). Whereas other factors linked to regulate AR activity such as IL6 [16] were not up-regulated (FIG. 8a). In line with this evidence, cytokine profile analysis in murine MDSCs showed that IL23 was the most over-expressed factor produced by these cells (FIG. 8b). Immunofluorescence and flow cytometry analyses further confirmed that tumor-infiltrating MDSCs expressed IL23 in vivo, with PMN-MDSCs infiltrating castration-resistant tumors expressing even higher levels of IL23 when compared to treatment naïve tumors (FIG. 2a-b). Of note, expression of CXCL5, a chemokine known to stimulate the chemotaxis of myeloid cells through the CXCR2 [17], was strongly up-regulated in castrated tumors compared to controls (FIG. 8a). This, together with the previous finding that CXCR2 inhibition efficiently decreases the recruitment of MDSCs in castrated mice, pointed at this factor as a major regulator of MDSCs recruitment in castrated tumors.

Figure 9:
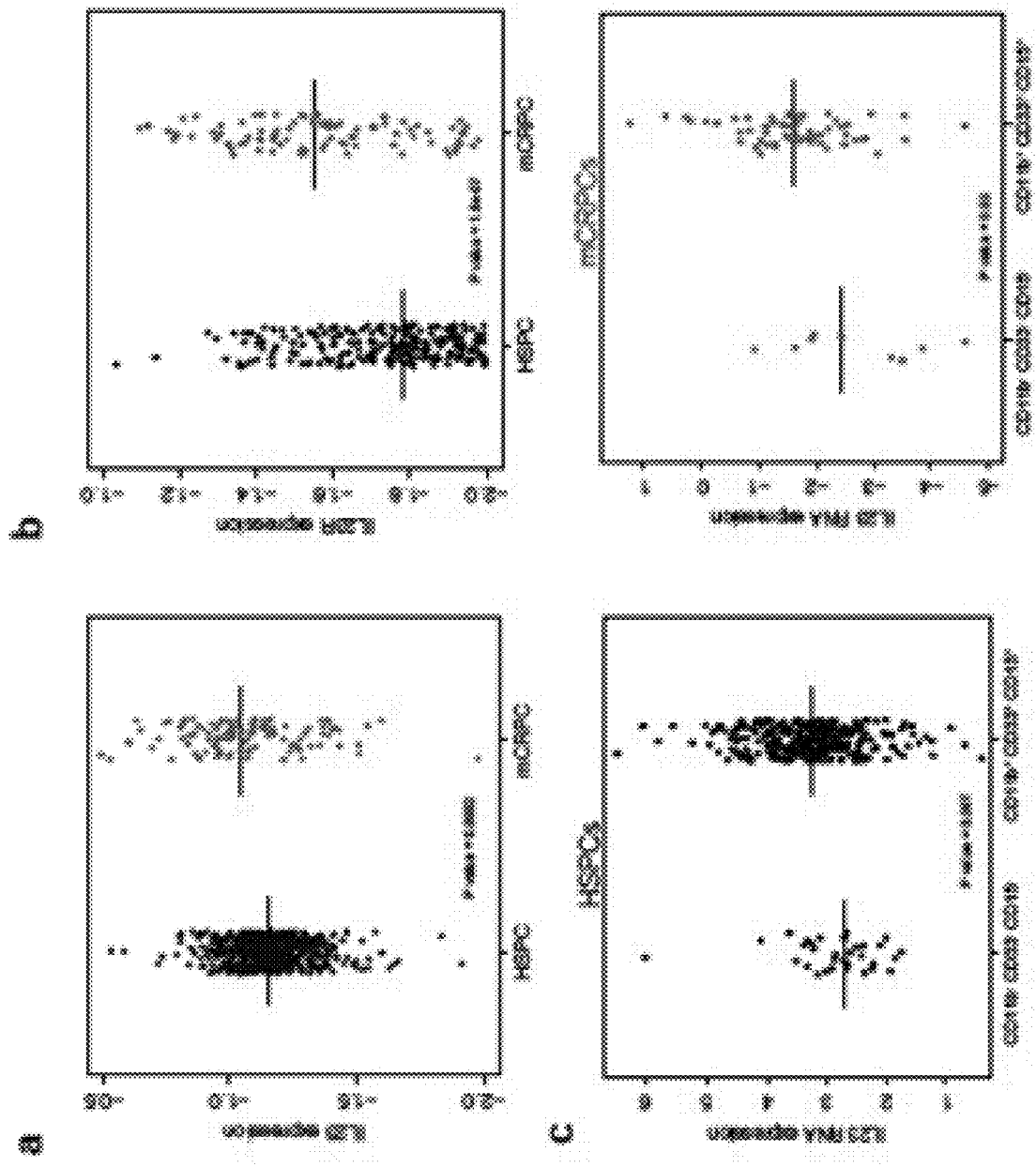

We then checked the status of IL23 receptor (IL23R) in sham and castrated Pten$^{pc-/-}$ tumors and we found that IL23R levels increased in tumor cells upon castration. This finding was further validated in TRAMP-C1 cells cultured in androgen deprivation conditions in vitro (FIG. 2c, FIG. 8cd). Notably, IL23 levels significantly decreased in castrated Pten$^{pc-/-}$ tumors depleted of MDSCs (FIG. 8e), demonstrating that IL23 in the tumor microenvironment of these mice derived from MDSCs. We next validated these findings in human prostate cancer patients. Quantification of IL23 in the plasma of CRPC patients revealed higher levels of IL23 than in HSPC patients (FIG. 2d; FIG. 8f). Moreover, tumor biopsies from CRPC patients had much higher IL23 and IL23R mRNA levels than tumor biopsies of treatment naïve patients (FIG. 9a-b). Finally, elevated IL23 mRNA levels were also associated with increased MDSC markers in CRPC biopsies (FIG. 9c). Overall, these data demonstrate that IL23 is elevated in both mouse and human CRPCs.

To functionally validate these findings, we cultured prostate tumor cells in the presence of C.M. of MDSCs from IL23 wild type (MDSCs$^{IL23wt}$) or IL23 knockout mice (MDSCs$^{IL23ko}$). While the C.M. of MDSCs$^{IL23wt}$ or treatment with recombinant IL23 promoted proliferation, survival and increased transcription of androgen receptor target genes in prostate tumor cells kept in F.A.D., the C.M. of MDSCs$^{IL23ko}$ was ineffective (FIG. 2e-h). Of note, the deletion of IL23 in MDSCs did not affect the levels of additional secreted factors in these cells (R2=0.94; FIG. 9d). Indeed, MDSCs$^{IL23wt}$ and MDSCs$^{IL23ko}$ cells had equal immunosuppression capability (FIG. 9d-e). These results were further validated in a subset of androgen-dependent organoids derived either from cancer patients or LNCaP cells kept in F.A.D and treated in presence or absence of human recombinant IL23 (FIG. 2i). Taken together, these findings identify IL23 as the MDSC-secreted factor that sustains cancer cell proliferation, survival, and transcription of AR target genes in prostate cancer cells cultured in F.A.D.

Figure 3:
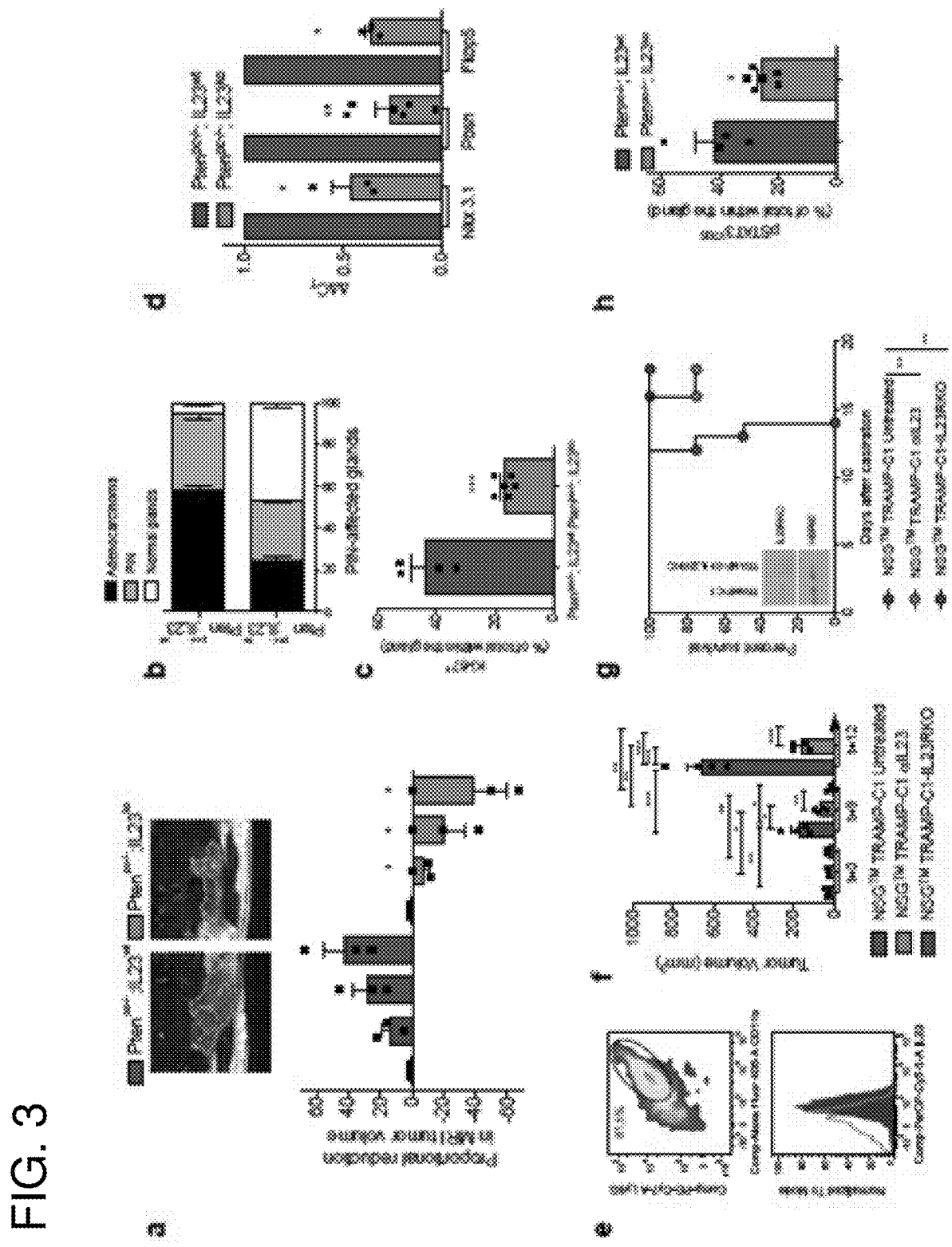
FIGS. 3A-3L. MDSCs regulate castration resistance through IL23 in vivo. a, Castrated-$Pten^{pc-/-}$ mice were lethally irradiated, transplanted with BM precursors depleted by T, B, and NK cells from IL23wt and IL23ko mice and monitored by MRI for tumor progression. MRIs of representative $Pten^{pc-/-}$; IL23wt and $Pten^{pc-/-}$; IL23ko mice at the completion of the study is reported (upper panels). Waterfall plot depicting proportional change in tumor response for $Pten^{pc-/-}$; IL23wt (n=3) and $Pten^{pc-/-}$; IL23ko (n=3) mice. Mean±SE. Statistical analyses (Unpaired Student t test): *P<0.05, One-way ANOVA: P=0.0008. b, Quantification of high grade (HG) or low grade (LG) prostatic intraepithelial neoplasia (PIN)-affected glands or normal glands in $Pten^{pc-/-}$; IL23wt (n=4) and $Pten^{pc-/-}$; IL23ko (n=6) mice. One tumor per mouse, three sections per mouse, 3 fields per section. c, Quantification of Ki-67 positive cells is reported as a percentage of total within the glands. One tumor per mouse, mean of three sections per mouse, ≥3 fields per section. Biological mean±SE. Pten$^{pc-/-}$; IL23wt (n=4) and Pten$^{pc-/-}$; IL23ko (n=6). Statistical analyses (Unpaired Student t test): **P<0.01. d, qRT-PCR analyses of the indicated genes in the prostate tumors of Pten$^{pc-/-}$; IL23wt (n=3) and Pten$^{pc-/-}$; IL23ko (n=3) mice at completion of the study. Data are reported as mean±SE. Statistical analyses (Paired Student t test): *P<0.05; **P<0.01. e-g, Six-week-old NSGTM males were challenged s.c. with TRAMP-C1 cells (n=4 per group) or TRAMP-C1-IL23RKO cells (n=5). When tumors reached≈30 mm³, mice were surgically castrated and treated with Isotype control (Untreated; n=4) or anti-IL23 antibody (αIL23; 100 ng/per mouse i.p. weekly; n=4) and monitored for tumor progression (t=days post-castration). e, Representative dot plot of CD11b$^+$ Ly6G$^+$ cells gated on CD45$^+$ cells within the tumor (Upper panel). CD11b$^+$ Ly6G$^+$ cells were also stained with anti-IL-23 antibodies (blue histogram) and analyzed by flow-cytometry; FMO (Fluorescence Minus One) sample was not stained for IL-IL23 (gray histogram) (Lower panel). f, Average tumor volume for each experimental group at the reported time points post-castration. Data are reported as mean±SE. Each dot represents an individual mouse. Statistical analyses (Unpaired Student t test): *P<0.05; P<0.01; *P<0.001. g, Survival curves are reported in Kaplan-Meier plot. Statistical analyses (Long-rank test): **P<0.01. WB for IL23R in TRAMP-C1 and TRAMP-C1 IL23RKO cell lines as insert. h, Quantification of pSTAT3Y705 positive cells is reported as a percentage of total within the glands of Ptenpc-/-; IL23wt (n=4) and Pten$^{pc-/-}$; IL23ko mice (n=6). One tumor per mouse, mean of three sections per mouse, ≥3 fields per section. Biological mean±SE. Statistical analyses (Unpaired Student t test): *P<0.05. i, Western blot for RORγ, pSTAT3Y705 and total STAT3 levels of prostate tumors of Pten$^{pc-/-}$; IL23wt (n=3) and Pten$^{pc-/-}$; IL23ko (n=3) mice. Loading control: anti-HSP90 antibody. j, Quantification is reported as mean±SE. Statistical analyses (Unpaired Student t test): P<0.01; *P<0.001. k, l, TRAMP-C1 prostate cancer cells were starved as reported in FIG. 1f and then kept in F.A.D., and cultured in presence of C.M. MDSCs or rIL23 with or without RORγ antagonist (αRORγ). k, Cell proliferation of TRAMPC1 cells after 72 h of co-culture (fold change compared with F.A.D. condition). l, qRT-PCR analyses of the indicated genes in TRAMP-C1 cells after 24 h of co-culture (fold change compared with F.A.D. condition). k, l, Aggregated data from three independent experiments are reported as mean±SE. Each dot represents a biological replicate. k, Statistical analyses (Unpaired Student t test): *P<0.05; P<0.01; *P<0.001. l, Statistical analyses (Paired Student t test between F.A.D. and the other group and Unpaired Student t test between all the others): *P<0.05; P<0.01; *P<0.001.
Figure 11:
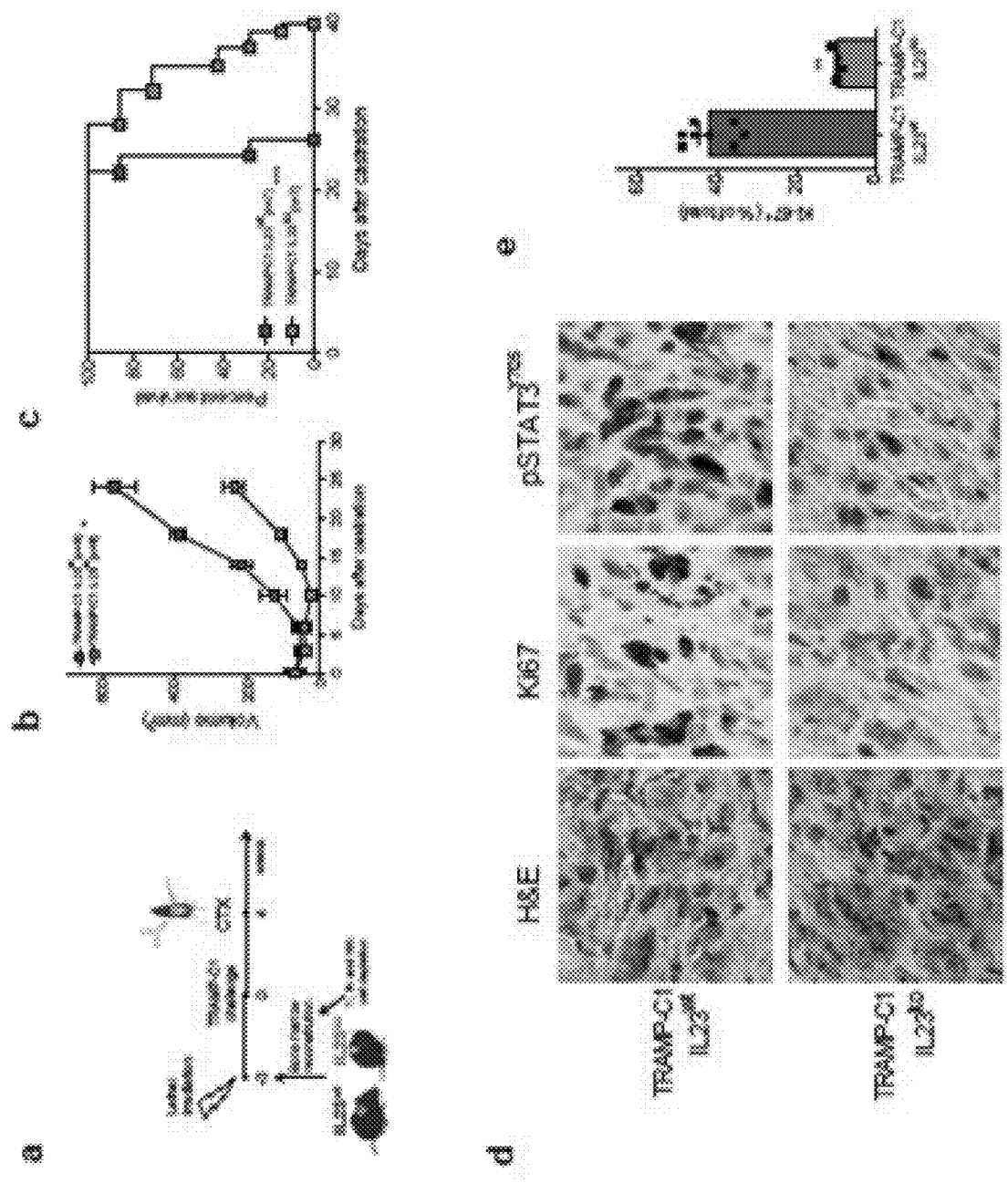

To determine whether MDSCs-derived IL23 promotes the emergence of CRPCs in vivo, we reconstituted lethally irradiated sham-operated or castrated-Pten$^{pc-/-}$ mice with BM precursors from IL23$^{wt}$ or IL23$^{ko}$ mice (yielding Pten$^{pc-/-}$; IL23$^{wt}$ mice and Pten$^{pc-/-}$; IL23$^{ko}$ mice) (FIG. 10a). Mice were reconstituted with BM deprived of T, B and NK cells. The absence of IL23 in the myeloid compartment led to a dramatic reduction in prostate cancer tumor volume specifically in castrated-Pten$^{pc-/-}$ mice (FIG. 10b; FIG. 3a), normalization of glands affected by prostate cancer and reduction of Ki-67 positive cells (FIG. 3b-c; FIG. 10c). Importantly, AR target genes were strongly down-regulated in Pten$^{pc-/-}$; IL23$^{ko}$ when compared to Pten$^{pc-/-}$; IL23$^{wt}$ prostate tumors (FIG. 3d). These data were also validated in TRAMP-C1 allograft mice reconstituted with IL23$^{wt}$ and IL23$^{ko}$ BM precursors (yielding TRAMP-C1 IL23$^{wt}$ and TRAMP-C1 IL23$^{ko}$ mice) (FIG. 11a). In TRAMP-C1 IL23$^{ko}$ mice, the absence of IL23 in the myeloid compartment significantly delayed the emergence of CRPC as demonstrated by the decreased tumor size, tumor cells proliferation and levels of AR target genes and provided a significant survival advantage to the mice IN TRAMP-C1 IL23$^{ko}$ mice (FIG. 11b-f). Critically, the IL23$^{ko}$ BM reconstitution did not affect the recruitment of MDSCs into the tumors and spleens of reconstituted mice (FIG. 11g-h). To unequivocally demonstrate that IL23 released by MDSCs confers castration resistance in prostate cancer independently of additional tumor-infiltrating immune subsets, we injected TRAMP-C1 cells in fully immunodeficient allografts (NSGTM: T, B and NK cells deficient, dendritic cells and macrophages defective). After tumor formation, mice were castrated and treated with isotype control (Untreated) or an antibody against IL23 (αIL23). Note that, the only immune population infiltrating TRAMP-C1-NSGTM tumors was positive for CD11b Ly6G and able to produce IL23 (FIG. 3e). αIL23 treatment significantly delayed the emergence of castration-resistant prostate cancer in treated mice (FIG. 3f). Indeed, when all the untreated mice were succumbed to the disease, all the treated mice were still alive (FIG. 3g). Of note, genetic inactivation of IL23R in TRAMP-C1-NSGTM allografts confirmed these results (FIG. 3f,g), demonstrating that MDSCs directly promote castration insensitivity by releasing IL23 in the tumor microenvironment.

IL-23 has been previously shown to regulate the activation of STAT3/RORγ expression in naive CD4 T cells [18-20], and both STAT3 and RORγ are reported to impact AR signaling in prostate cancer [21,22]. We, therefore, evaluated whether IL23 secreted by MDSCs could regulate the STAT3/RORγ axis in prostate cancer by acting in a non-cell autonomous manner. Inactivation of IL23 in the myeloid compartment of castrated Pten$^{pc-/-}$ mice significantly decreased the overall tumor levels of pSTAT3 and RORγ in vivo (FIG. 3h-j; FIG. 10c). These data were also validated in the TRAMP-C1 model (FIG. 11d, i-k). RORγinhibition in vitro also abrogated the proliferative advantage conferred by the C.M. of MDSCs in TRAMP-C1 cells kept in F.A.D., thereby inhibiting the transcription of the full-length form of the AR, its constitutive active variant (ARv4), and AR target genes induced by MDSCs and IL23 treatment in TRAMP-C1 cells kept in F.A.D. (FIG. 3k,l). Altogether, these data demonstrate that the IL23 released by MDSCs into the tumor microenvironment acts directly on the pSTAT3/RORγaxis activating the transcription of the AR and its target genes, favoring the proliferation and survival of the tumor cells also in androgen ablation condition.

To evaluate the therapeutic relevance of our findings, we next assessed whether IL23 inhibition by antibody blockade could revert castration resistance in Pten$^{pc-/-}$ mice mimicking a clinical relevant setting [1]. Anti-IL23 blocking antibodies are currently used in the clinic for the treatment of autoimmune diseases [23] and are well tolerated even in patients treated for long period of time [24].

Figure 4:
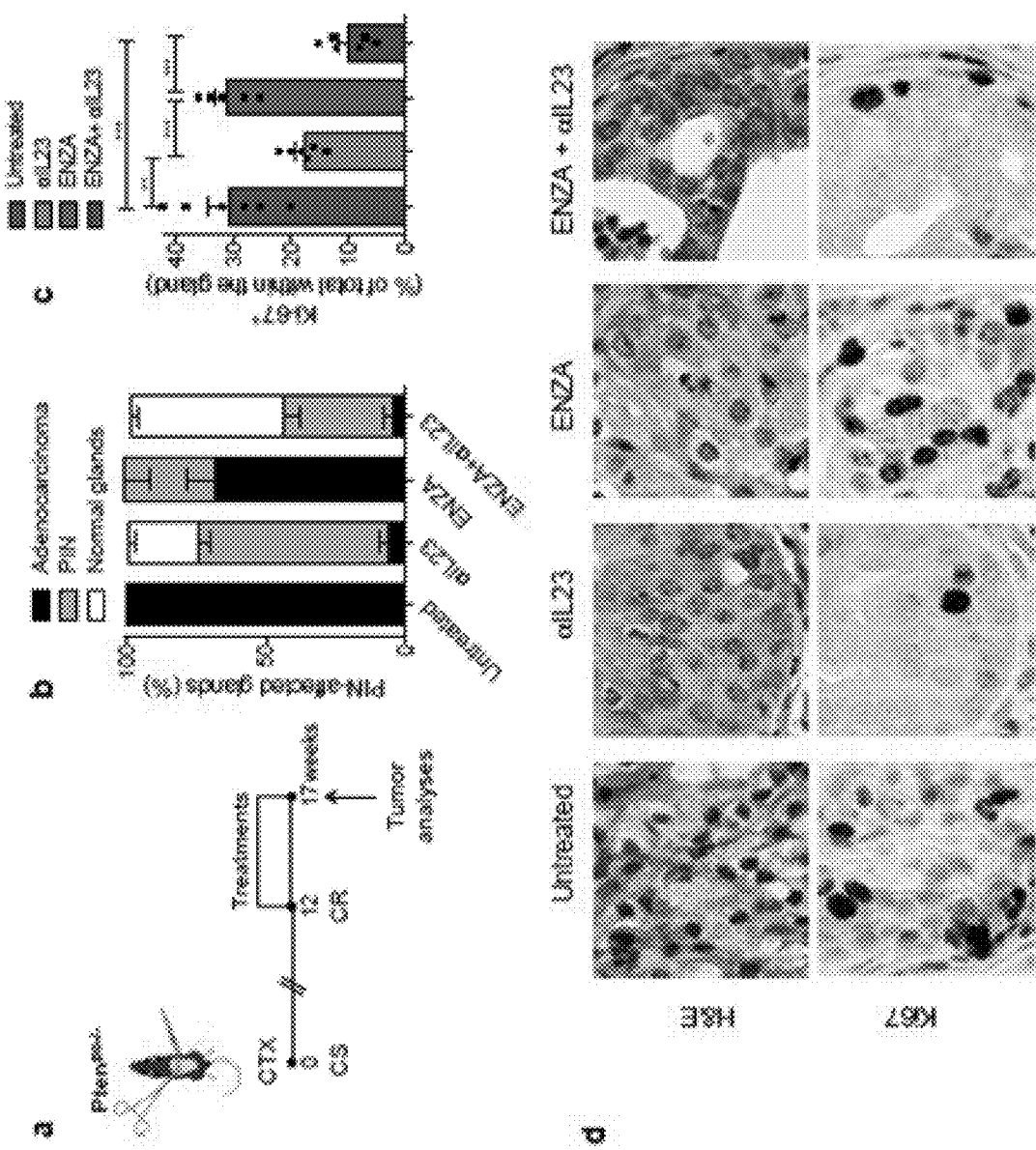
FIGS. 4A-4G. IL23 inhibition synergizes with standard androgen deprivation therapy in vivo. a, Experimental set-up. Pten$^{pc-/-}$ mice were surgical castrated, when castration resistance occurred (12 weeks after castration), they were randomly enrolled in the preclinical trial. Treatments: Isotype control (Untreated; n=6), anti-IL23 antibody (αIL23; 100 ng/per mouse i.p. weekly; n=6), Enzalutamide (ENZA, 30 mg/kg/day administered daily by oral gavage on a Monday to Friday schedule, n=5), and Enzalutamide in combination with anti-IL23 antibody (ENZA+αIL23, n=6). b, Quantification of adenocarcinoma or PIN-affected glands or normal glands in response to treatment is reported. One tumor per mouse, three sections per mouse, ≥3 fields per section. c, Quantification of Ki-67 reported as a percentage of total within the glands. One tumor per mouse, three sections per mouse, ≥3 fields per section. Mean±SE. Each dot represents an individual mouse. Statistical analyses (Unpaired Student t test): P<0.01; *P<0.001. d, H&E and Ki-67 immunohistochemical staining (Ki-67 brown; nuclei, blue) of representative castrated-Pten mice treated with αIL23, ENZA or both at completion of the study. Original magnification, ×400. e, qRT-PCR analyses of the indicated genes in the prostate tumors of castrated-Pten$^{pc-/-}$ mice at completion of the preclinical trial. Data are reported as mean±SE. Each dot represents an individual mouse. Statistical analyses (Paired Student t test): *P<0.05; *P<0.001. f, Cleaved-Caspase3 immunohistochemical staining (Cleaved-Casp 3 brown; nuclei, blue) of representative castrated-Pten$^{pc-/-}$ mice treated with αIL23, ENZA or both one week after the start of the treatments. Original magnification, ×400. g, Quantification of Cleaved-Casp 3 reported as a percentage of total within the glands. N=3, one tumor per mouse, three sections per mouse, ≥3 fields per section. Mean±SE. Statistical analyses (Unpaired Student t test): P<0.01; ***P<0.001.

Hence, we treated Pten$^{pc-/-}$ mice who have become resistant to surgical castration with a αIL23 in combination with enzalutamide (ENZA), the standard of care for patients insensitive to first line ADT1 (FIG. 4a). Our preclinical study showed that αIL23 synergizes with ENZA (FIG. 4b). Indeed, in mice treated with αIL23 and ENZA, we observed a normalization of prostate glands affected by cancer (FIG. 4b; FIG. 12a), decreased tumor volume (FIG. 12b) and proliferation (FIG. 4c-d) whereas in mice treated with ENZA alone the treatment was ineffective. These changes were associated with a robust inhibition of the AR activity and apoptosis (FIG. 4e-g). Taken together, these data demonstrate that anti-IL23 treatment reverts castration resistance in prostate cancer enhancing the efficacy of ENZA.

In conclusion, we have identified MDSC-derived IL23 as a novel driver of CRPC adding novel insights on the mechanism by which prostate tumor cells become insensitive to androgen deprivation. These data also add a new knowledge on the role played by MDSCs in cancer, describing a new unexpected function for this immune subset. Finally, our work proves through preclinical studies that inhibition of IL23 synergizes with the standard-of-care treatments for CRPC offering a solid basis for novel therapeutic drug combination strategies in the clinic for this commonest of male cancers (FIG. 12c). IL23 antibodies may be used to prevent the emergence of CRPC in hormone sensitive prostate cancer patients or to revert castration resistance in patients treated with enzalutamide.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

REFERENCES

[1] Watson, P. A., Arora, V. K. & Sawyers, C. L. Emerging mechanisms of resistance to androgen receptor inhibitors in prostate cancer. *Nat Rev Cancer* 15, 701-711, doi:10.1038/nrc4016 (2015).

[2] Bianchini, D. et al. Antitumour activity of enzalutamide (MDV3100) in patients with metastatic castration-resistant prostate cancer (CRPC) pre-treated with docetaxel and abiraterone. *Eur J Cancer* 50, 78-84, doi:10.1016/j.ejca.2013.08.020 (2014).

[3] Zhang, T. et al. Exploring the Clinical Benefit of Docetaxel or Enzalutamide After Disease Progression During Abiraterone Acetate and Prednisone Treatment in Men With Metastatic Castration-Resistant Prostate Cancer. *Clin Genitourin Cancer* 13, 392-399, doi:10.1016/j.clgc.2015.01.004 (2015).

[4] Badrising, S. et al. Clinical activity and tolerability of enzalutamide (MDV3100) in patients with metastatic, castration-resistant prostate cancer who progress after docetaxel and abiraterone treatment. *Cancer* 120, 968-975, doi:10.1002/cncr.28518 (2014).

[5] Noonan, K. L. et al. Clinical activity of abiraterone acetate in patients with metastatic castration-resistant prostate cancer progressing after enzalutamide. *Ann Oncol* 24, 1802-1807, doi:10.1093/annonc/mdt138 (2013).

[6] Schrader, A. J. et al. Enzalutamide in castration-resistant prostate cancer patients progressing after docetaxel and abiraterone. *Eur Urol* 65, 30-36, doi:10.1016/j.eururo.2013.06.042 (2014).

[7] Quail, D. F. & Joyce, J. A. Microenvironmental regulation of tumor progression and metastasis. *Nat Med* 19, 1423-1437, doi:10.1038/nm.3394 (2013).

[8] Gabrilovich, D. I. & Nagaraj, S. Myeloid-derived suppressor cells as regulators of the immune system. *Nat Rev Immunol* 9, 162-174, doi:10.1038/nri2506 (2009).

[9] Hossain, D. M. et al. TLR9-Targeted STAT3 Silencing Abrogates Immunosuppressive Activity of Myeloid-Derived Suppressor Cells from Prostate Cancer Patients. *Clin Cancer Res* 21, 3771-3782, doi:10.1158/1078-0432.CCR-14-3145 (2015).

[10] Lu, X. et al. Effective combinatorial immunotherapy for castration-resistant prostate cancer. *Nature* 543, 728-732, doi:10.1038/nature21676 (2017).

[11] Murdoch, C., Muthana, M., Coffelt, S. B. & Lewis, C. E. The role of myeloid cells in the promotion of tumour angiogenesis. *Nat Rev Cancer* 8, 618-631, doi:10.1038/nrc2444 (2008).

[12] Di Mitri, D. et al. Tumour-infiltrating Gr-1+ myeloid cells antagonize senescence in cancer. *Nature* 515, 134-137, doi:10.1038/nature13638 (2014).

[13] Bronte, V. et al. Recommendations for myeloid-derived suppressor cell nomenclature and characterization standards. *Nat Commun* 7, 12150, doi:10.1038/ncomms12150 (2016).

[14] Lunardi, A. et al. A co-clinical approach identifies mechanisms and potential therapies for androgen deprivation resistance in prostate cancer. *Nat Genet* 45, 747-755, doi:10.1038/ng.2650 (2013).

[15] Clinical Trial NCT03177187. https://clinicaltrials.gov/ct2/show/NCT03177187.

[16] Lee, G. T. et al. Bone morphogenetic protein-6 induces castration resistance in prostate cancer cells through tumor infiltrating macrophages. *Cancer Sci* 104, 1027-1032, doi:10.1111/cas.12206 (2013).

[17] Persson, T. et al. Expression of the neutrophil-activating CXC chemokine ENA-78/CXCL5 by human eosinophils. *Clin Exp Allergy* 33, 531-537 (2003).

[18] Durant, L. et al. Diverse targets of the transcription factor STAT3 contribute to T cell pathogenicity and homeostasis. *Immunity* 32, 605-615, doi:10.1016/j.immuni.2010.05.003 (2010).

[19] Kastelein, R. A., Hunter, C. A. & Cua, D. J. Discovery and biology of IL-23 and IL-27: related but functionally distinct regulators of inflammation. *Annu Rev Immunol* 25, 221-242, doi:10.1146/annurev.immunol.22.012703.104758 (2007).

[20] Zhou, L. et al. IL-6 programs T(H)-17 cell differentiation by promoting sequential engagement of the IL-21 and IL-23 pathways. *Nat Immunol* 8, 967-974, doi:10.1038/ni1488 (2007).

[21] Chen, T., Wang, L. H. & Farrar, W. L. Interleukin 6 activates androgen receptor-mediated gene expression through a signal transducer and activator of transcription 3-dependent pathway in LNCaP prostate cancer cells. *Cancer Res* 60, 2132-2135 (2000).

[22] Wang, J. J. et al. ROR-gamma drives androgen receptor expression and represents a therapeutic target in castration-resistant prostate cancer (vol 22, pg 488, 2016). *Nature Medicine* 22, 692-692, doi:10.1038/nm0616-692b (2016).

[23] Campa, M., Mansouri, B., Warren, R. & Menter, A. A Review of Biologic Therapies Targeting IL-23 and IL-17 for Use in Moderate-to-Severe Plaque Psoriasis. *Dermatol Ther (Heidelb)* 6, 1-12, doi:10.1007/s13555-015-0092-3 (2016).

[24] Gordon, K. B. et al. A Phase 2 Trial of Guselkumab versus Adalimumab for Plaque Psoriasis. *N Engl J Med* 373, 136-144, doi:10.1056/NEJMoa1501646 (2015).

[25] Marigo, I. et al. Tumor-induced tolerance and immune suppression depend on the C/EBPbeta transcription factor. *Immunity* 32, 790-802, doi:10.1016/j.immuni.2010.05.010 (2010).

[26] Lechner, M. G., Liebertz, D. J. & Epstein, A. L. Characterization of cytokine-induced myeloid derived suppressor cells from normal human peripheral blood mononuclear cells. *J Immunol* 185, 2273-2284, doi:10.4049/jimmunol.1000901 (2010).

[27] Robinson, D. et al. Integrative clinical genomics of advanced prostate cancer. *Cell* 161, 1215-1228, doi:10.1016/j.cell.2015.05.001 (2015).

[28] Kim, D. et al. TopHat2: accurate alignment of transcriptomes in the presence of insertions, deletions and gene fusions. *Genome Biol* 14, R36, doi:10.1186/gb-2013-14-4-r36 (2013).

[29] Trapnell, C. et al. Differential gene and transcript expression analysis of RNA-seq experiments with TopHat and Cufflinks. *Nat Protoc* 7, 562-578, doi:10.1038/nprot.2012.016 (2012).

[30] Drost, J. et al. Organoid culture systems for prostate epithelial and cancer tissue. *Nat Protoc* 11, 347-358, doi:10.1038/nprot.2016.006 (2016).

The invention claimed is:

1. A method of reversing resistance to androgen deprivation therapy (ADT) in a prostate cancer, comprising:
   identifying a prostate cancer in a mammalian patient which prostate cancer has developed resistance to the anti-tumor effects of ADT;
   administering a therapeutically effective amount of an antibody or antibody fragment that binds the p19 subunit of IL-23 to the patient; and
   administering ADT to the patient, wherein said ADT comprises an antiandrogen therapy selected from the group consisting of enzalutamide, cyproterone acetate, flutamide, nilutamide, bicalutamide, abiraterone acetate, seviteronel, apalutamide, darolutamide, galeterone, leuprolide, goserelin, triptorelin, histrelin, degarelix, and orchiectomy surgery.

2. The method of claim 1, further comprising simultaneous, sequential or separate administration of an inhibitor of interleukin 8 receptor (CXCR2), an inhibitor of RAR-related orphan receptor gamma (RORγ) and/or an inhibitor of Signal transducer and activator of transcription 3 (STAT3) to said patient.

3. The method of claim 1, wherein the prostate cancer comprises castration resistant prostate cancer (CRPC).

4. The method of claim 1, wherein said antibody or antibody fragment is sufficient to sensitize the prostate cancer to the anti-tumor effects of said ADT.

5. The method of claim 1, wherein the antibody or antibody fragment is selected from the group consisting of: guselkumab, risankizumab, and tildrakizumab.

6. The method of claim 1, wherein the method comprises administration of simultaneous, sequential or separate administration of said antibody or antibody fragment and enzalutamide.

7. The method of claim 2, wherein the inhibitor of CXCR2 comprises AZD5069.

8. The method of claim 2, wherein said inhibitor of RORγ comprises an antibody or antibody fragment that selectively binds RORγ.

9. The method of claim 1, wherein administering the antibody or antibody fragment that binds the p19 subunit of IL-23 and the ADT to the patient is simultaneous, sequential, or separate.

* * * * *